US009539353B2

(12) United States Patent
Kim et al.

(10) Patent No.: US 9,539,353 B2
(45) Date of Patent: Jan. 10, 2017

(54) OLFACTORY DISPLAY AND FRAGRANCE SOURCE CARTRIDGE USED THEREIN

(71) Applicant: National Institute of Information and Communications Technology, Tokyo (JP)

(72) Inventors: Dong Wook Kim, Tokyo (JP); Hiroshi Ando, Tokyo (JP)

(73) Assignee: National Institute of Information and Communications Technology, Tokyo (JP)

( * ) Notice: Subject to any disclaimer, the term of this patent is extended or adjusted under 35 U.S.C. 154(b) by 74 days.

(21) Appl. No.: 14/440,558

(22) PCT Filed: Oct. 21, 2013

(86) PCT No.: PCT/JP2013/078448
§ 371 (c)(1),
(2) Date: May 4, 2015

(87) PCT Pub. No.: WO2014/069269
PCT Pub. Date: May 8, 2014

(65) Prior Publication Data
US 2015/0283282 A1 Oct. 8, 2015

(30) Foreign Application Priority Data
Nov. 2, 2012 (JP) ................................ 2012-243025

(51) Int. Cl.
*A61L 9/12* (2006.01)
*B01F 3/04* (2006.01)
(Continued)

(52) U.S. Cl.
CPC .. *A61L 9/12* (2013.01); *A61L 2/00* (2013.01); *A61L 9/00* (2013.01); *A61L 9/125* (2013.01);
(Continued)

(58) Field of Classification Search
CPC .............. B01F 3/04; A61L 9/12; A61L 9/125; A62B 7/08
(Continued)

(56) References Cited

U.S. PATENT DOCUMENTS 4,571,485 A 2/1986 Spector .......................... 219/276
6,712,287 B1 3/2004 Le Pesant et al. ............... 239/67
(Continued)

FOREIGN PATENT DOCUMENTS

CN 1781133 5/2006 ............. G09F 15/00
CN 101121037 2/2008 ............... A61L 9/03
(Continued)

OTHER PUBLICATIONS

Communication Pursuant to Rule 164(1) EPC, dated Mar. 8, 2016, issued by the European Patent Office in Applicant's corresponding European Patent Application No. 13851099.5, filed on Oct. 21, 2013, a Supplementary Partial European Search Report, the European Search Opinion and Annex to the European Search Report, all dated Feb. 25, 2016, issued by the European Patent Office in Applicant's aforementioned corresponding European Patent Application No. 13851099.5, filed on Oct. 21, 2013.
International Search Report, in English, dated Nov. 12, 2013, and the Written Opinion of the International Searching Authority (in English), dated Nov. 11, 2013, issued from Applicant's corresponding PCT Application No. PCT/JP2013/078448, filed on Oct. 21, 2013, each of which being from the World Intellectual Property Organization (WIPO).

*Primary Examiner* — Robert A Hopkins
(74) *Attorney, Agent, or Firm* — Bodner & O'Rourke, LLP; Gerald T. Bodner; Christian P. Bodner

(57) ABSTRACT

An olfactory display 10 includes a display main body 12 and a fragrance source cartridge 14, and presents a fragrance to a range bounded in terms of time and space. A cartridge accommodation room (24) of the display main body 12 and a container main body (80) of the fragrance source cartridge 14 are formed with inclined surfaces 46 and 84 inclined with respect to an insertion direction of the fragrance source cartridge 14, and a force that pushes in the fragrance source (Continued)

cartridge 14 acts in a direction that an open air inlet 82 is pressed to an air supply port 54 side. Accordingly, adhesiveness of a coupling portion of the air supply port 54 and the open air inlet 82 increases, and therefore, capability of an airflow source 26 is used to the utmost, and a high static pressure is generated in the fragrance source cartridge 14 for a short time.

8 Claims, 11 Drawing Sheets

(51) Int. Cl.
    *F04B 43/04*     (2006.01)
    *A61L 2/00*     (2006.01)
    *A61L 9/00*     (2006.01)

(52) U.S. Cl.
    CPC ............... *B01F 3/04* (2013.01); *F04B 43/046* (2013.01); *A61L 2209/132* (2013.01); *A61L 2209/133* (2013.01)

(58) Field of Classification Search
    USPC ................ 261/30, 94, 95, DIG. 88; 422/124
    See application file for complete search history.

(56) References Cited

U.S. PATENT DOCUMENTS

| | | | |
|---|---|---|---|
| 6,713,024 B1 * | 3/2004 | Arnell | A61L 9/125 |
| | | | 239/57 |
| 7,363,737 B2 | 4/2008 | Benalikhoudja | 40/407 |
| 8,821,802 B2 * | 9/2014 | Haran | A61L 9/122 |
| | | | 422/120 |

FOREIGN PATENT DOCUMENTS

| | | | | |
|---|---|---|---|---|
| JP | 2004-121594 | | 4/2004 | ............... A61L 9/12 |
| JP | 2005-304609 | | 11/2005 | ............ A16M 15/00 |
| JP | 2008-257216 | | 10/2008 | ............ G09F 19/00 |
| JP | 2009-265453 | | 11/2009 | ............ G09F 19/00 |
| JP | 2012-173381 | | 9/2012 | ............ G09F 19/00 |
| JP | 2013-167741 | | 8/2013 | ............ G09F 19/00 |
| WO | WO 2004/086336 | | 10/2004 | ............ G09F 15/00 |

* cited by examiner

INSERTION DIRECTION

OLFACTORY DISPLAY AND FRAGRANCE SOURCE CARTRIDGE USED THEREIN

TECHNICAL FIELD

The present invention relates to an olfactory display and a fragrance source cartridge used therein, and more specifically, an olfactory display that presents a fragrance within a range bounded in terms of time and space, and a fragrance source cartridge used therein.

BACKGROUND ART

Recently, there are proposed various kinds of olfactory displays which present a fragrance (olfactory information) in cooperation with an audio-visual display of a television, a personal computer, etc. for a purpose of information presentation by which a high presence, a high immersion feeling and so on can be applied to a user. Here, in a case where a specific fragrance is to be presented for a certain degree of a long period of time, it is sufficient to simply diffuse a fragrance in a space. However, in order to present a fragrance in synchronization with a scene change of a content displayed by an audio-visual display, for example, a temporal control (temporal locality) of fragrance presentation becomes needed. Furthermore, in order to present a fragrance to only a target person, for example, a spatial control (spatial locality) of fragrance presentation becomes needed. Furthermore, if the temporal locality and the spatial locality for the fragrance presentation are implemented, not only an aromatic material to be used can be greatly saved but also a problem of a lingering fragrance can be solved. From these, an olfactory display which presents a fragrance controllable in terns of time and space, that is, an olfactory display which can present a fragrance within a range bounded in terms of time and space is expected.

The patent literature 1 discloses an example of a conventional olfactory display. The aroma generating apparatus of the patent literature 1 comprises an aromatic material accommodating portion which accommodates a solid-like aromatic material, and pumps are provided at an inlet side and an outlet side of the aromatic material accommodating portion, respectively. In generating the fragrance, the inlet side pump is rotated to send an air into the aromatic material accommodating portion, whereby an air (fragrance) to which the aroma is added can be pushed out of the aromatic material accommodating portion, and at the same time, by rotating the outlet side pump, the fragrance is discharged to an external from the fragrance discharging port.

Furthermore, another example of a conventional olfactory display is disclosed in the patent literature 2. A gas discharge apparatus of the patent literature 2 is an apparatus that is incorporated in a public information presenting apparatus to present a fragrance corresponding to a picture, and shoots a vortex ring having a fragrance component according to a principle of an air canon. Specifically, the gas discharge apparatus of the patent literature 2 comprises a plurality of fragrance discharge pipes having tip ends inserted between luminescence display elements. On an outer peripheral surface, there is provided with a fragrance store mechanism (fragrance source) via an airflow control plate for opening and closing a fragrance supply hole. At a rear end portion of the fragrance discharge pipe, there is an atmospheric layer that is provided with a bimorph piezoelectric device. Then, in shooting the fragrance, by rendering the fragrance supply hole in an opened state and by reducing an internal volume of the atmospheric layer by bending the bimorph piezoelectric inwardly, a vortex-ring-like mass of fragrance is shot from the fragrance discharge pipe.

However, in the art of the patent literature 1, the fragrance is merely pushed-out to the outside from the aromatic material accommodating portion by the rotation of a rotor of the pump, that is, the fragrance is merely diffused to a surrounding space, and therefore, the spatial control of the fragrance presentation is not considered. That is, the presentation of the fragrance within a range bounded in terms of space is not implemented. Furthermore, since structure is complex, there is a limit for a miniaturization.

Furthermore, in the technology of the patent literature 2, since a mass of fragrance is discharged by the principle of the air cannon, only momentary presentation of the fragrance can be performed, and therefore, it is impossible to perform continuous presentation of the fragrance not of pulsatile motion. Furthermore, since structure is complicated, there is a limit in a miniaturization, such as arranging the fragrance source outside a main body portion of a gas discharge apparatus consisting of the fragrance discharge pipe and the atmospheric layer.

Then, the inventors et al. proposed in the patent literature 3 an olfactory display capable of presenting a plurality of fragrances in a controllable manner in terms of time and space while attaining miniaturization of the apparatus. Specifically, the olfactory display of the patent literature 3 comprises a housing that is formed with a plurality of fragrance chambers divided by partitions. In each fragrance chamber, a solid-like fragrance source is accommodated and an airflow source comprising a diaphragm that is adhered with a piezoelectric device is provided. Furthermore, each fragrance chamber is communicated with an emission port via an individual fragrance path, and respective fragrance paths are joined to each other at a position near the emission port to form a single common path, and Venturi tube structure is provided in a joining portion.

Patent Literature 1: Japanese Patent Application Laying-Open No. 2004-121594 [A61 L 9/12]

Patent Literature 2: Japanese Patent Application Laying-Open No. 2008-257216 [G09 F 19/00]

Patent Literature 3: Japanese Patent Application Laying-Open No. 2012-30611 [A61L 9/12]

SUMMARY OF THE INVENTION

Problem to be Solved by the Invention

Since innumerable fragrances exist in the world, an olfactory display capable of presenting all the fragrances that exist innumerably is desired ultimately. Since the fragrance source stored in the fragrance chamber is exchangeable in the technology of the patent literature 3, it is possible to present innumerable fragrances by replacing a fragrance source.

However, with the technology of the patent literature 3, since the fragrance source is directly enclosed in the fragrance chamber of the apparatus, if a predetermined time period elapses, a fragrance component adheres to an inner wall surface of the fragrance chamber. Therefore, when replacing the fragrance source in the fragrance chamber with a fragrance source having another kind of fragrance component, there is a possibility that fragrance components are mixed with each other and thus a fragrance changes. Furthermore, there is a limit also in increasing the number of fragrance chambers to present more many kinds of fragrances from a viewpoint of a miniaturization of the apparatus. Therefore, in the technology of the patent literature 3, it is difficult to present various kinds of fragrances adequately, while only fragrances of a plurality of defined patterns can be presented.

Therefore, it is a primary object of the present invention to provide a novel olfactory display and fragrance source cartridge used therein.

It is another object of the present invention to provide an olfactory display and fragrance source cartridge used therein, capable of presenting more kinds of fragrances within a range bounded in terms of time and space while retaining miniaturization and simplicity.

The present invention employs following features in order to solve the above-described problems. It should be noted that reference numerals and the supplements inside the parentheses show one example of a corresponding relationship with the embodiments described later for easy understanding of the present invention, and do not limit the present invention.

A first invention is an olfactory display that includes a display main body and a fragrance source cartridge, and presents a fragrance within a range bounded in terms of time and space, wherein the display main body comprises a housing having an emission port in a center portion in a front side; a plurality of cartridge accommodation rooms that are formed by dividing an internal space of the housing by radial partitions, each of the cartridge accommodation rooms having an air supply port and an air discharge port; a communicating hole that is provided in the housing to make respective air discharge ports communicate with the emission port; cartridge exchange portions each formed in each of the cartridge accommodation rooms; and a plurality of airflow sources that are provided in the cartridge accommodation rooms, each of the airflow sources sending an air into the inside of the fragrance source cartridge that is accommodated in the cartridge accommodation room from the air supply port with using a diaphragm having a piezoelectric device, and each of the fragrance source cartridges comprises a container main body that has an outer shape conformed to an inner shape of the cartridge accommodation room, and is formed with an air inlet in a position corresponding to the air supply port and a fragrance outlet in a position corresponding to the air discharge port; and a solid-like fragrance source stored within the container main body, and the inner shape of the cartridge accommodation room and the outer shape of the container main body respectively have inclined surfaces inclined with respect to an insertion direction of the fragrance source cartridge.

In the first invention, the olfactory display (10) includes the display main body (12) and the fragrance source cartridge (14), and presents a fragrance within the range bounded in terms of time and space in conjunction with audiovisual displays such as a personal computer, television, etc.

In the housing (20) of the display main body, there are formed with a plurality of cartridge accommodation rooms (24) that are divided by the radial partitions (22), and in each of the cartridge accommodation room, the air supply port (54) and the air discharge port (50) are formed. The respective air discharge ports communicate with the emission port (16) via the communicating holes (42). Furthermore, an individual airflow source (26) is provided in each of the cartridge accommodation rooms. The airflow source comprises the diaphragm that the piezoelectric device (56) adheres, and when a high frequency alternating voltage is applied to the piezoelectric device, the diaphragm is vibrated, whereby airflow can be generated. Furthermore, the cartridge exchange portion (38) is formed in each cartridge accommodation room, and via this cartridge exchange portion, a fragrance source cartridge is accommodated inside the cartridge accommodation room attachably and detachably.

On the other hand, the fragrance source cartridge comprises the container main body (80) having the outer shape to be conformed to the inner shape of the cartridge accommodation room. The container main body is formed with the open air inlet (82) in the position corresponding to the air supply port of the cartridge accommodation room and the fragrance outlet (88) in the position corresponding to the air discharge port of the cartridge accommodation room. Furthermore, in the container main body, the solid-like fragrance source (90) is stored.

Then, the inclined surfaces (46, 92) inclines inwardly with respect to the insertion direction of the fragrance source cartridge into the cartridge accommodation room are formed on the inner surface of the cartridge accommodation room, and the inclined surfaces (84, 94) are also formed on the outer surface of the container main body corresponding to them. Since such inclined structure, if the fragrance source cartridge is pushed into the cartridge accommodation room, it rendered in a state where the fragrance source cartridge is fit to the cartridge accommodation room (fit state), a force in pushing the fragrance source cartridge (a force in the insertion direction) is held so as to act as a force pressing the inclined surfaces of fragrance source cartridge against the inclined surfaces of the cartridge accommodation room. Accordingly, since an adhesiveness of a coupling portion of the air supply port of the display main body and the air inlet of the fragrance source cartridge increases, a capability of the airflow source is used to the utmost, and therefore, a high static pressure is generated in the fragrance source cartridge for a short time.

According to the first invention, since a cartridge system that a fragrance source cartridge is accommodated attachably and detachably in the display main body, it is constructed that the cartridge is used for each fragrance, and therefore, various kinds of fragrances can be presented without causing confusion of a fragrance component. Furthermore, when adopting the cartridge system, in order to make the air supply port and the air inlet adequately adhere, there are provided with the inclined structure in the cartridge accommodation room and the fragrance source cartridge. That is, it becomes possible to make the air supply port and the air inlet adequately adhere with simple structure that the inclined structure is provided without providing with a complicated mechanism. Therefore, it is possible to present various kinds of fragrances within a range bounded in terms of time and space while retaining the miniaturization and simplicity.

A second invention is according to the first invention, wherein the airflow source is arranged to constitute a part of the partition and the air supply port is formed on the partition, and the cartridge exchange portion is formed on a side wall of the housing.

In the second invention, the airflow source (26) is arranged to constitute a part of the partition (22), and the air supply port (54) is formed in this partition. Furthermore, the cartridge exchange portion (38) is formed on the side wall (32) of the housing (20). That is, the fragrance source cartridge (14) is inserted from the housing side, and the inclined surfaces (46, 84) are formed to be inclined toward a center axis (48) side.

According to the second invention, it becomes easy to provide a cover in each cartridge exchange portion individually, and individually exchange of a fragrance source cartridge becomes simple.

A third invention is according to the first invention, wherein the airflow source is arranged to constitute a part of the partition and the air supply port is formed on the partition, and the cartridge exchange portion is formed on a front wall or a rear wall of the housing.

In the third invention, the airflow source (26) is arranged to constitute a part of the partition (22), and the air supply port (54) is formed on this partition. Furthermore, the cartridge exchange portion (38) is formed on the front wall (34) or the rear wall (30) of the housing (20). That is, the fragrance source cartridge (14) is inserted from the front or rear side of the housing, and the inclined surfaces (92, 94) are formed to be inclined toward the rear or the front side.

A fourth invention is according to the first invention, wherein the airflow source is arranged to constitute a part of a side wall and the air supply port is formed on the side wall, and the cartridge exchange portion is formed on a front wall or a rear wall of the housing.

In the fourth invention, the airflow source (26) is arranged to constitute a part of the side wall (32), and the air supply port (54) is formed on this side wall. Furthermore, the cartridge exchange portion (38) is formed on the front wall (34) or the rear wall (30) of the housing (20). That is, the fragrance source cartridge (14) is inserted from the front or the rear of the housing, and the inclined surfaces (92, 94) are formed to be inclined toward of the rear or the front side.

According to the fourth invention, since the airflow source is provided on the side wall, it is possible to make thickness of the partition thin and a cross section of a central coupling portion of the partitions. Accordingly, since the fragrance outlet can be formed in a position nearer the emission port, it is possible to make the fragrance outlet and the emission port communicate with each other in more linearly.

A fifth invention is according to any one of the first to fourth inventions, and further comprises a cover that is provided in the cartridge exchange portion and pushes the fragrance source cartridge in the insertion direction when the fragrance source cartridge is accommodated in the cartridge accommodation room.

In the fifth invention, the cartridge exchange portion (38) is provided with the cover (32b, 34) that pushes a tail end of the fragrance source cartridge in the insertion direction in a state where the fragrance source cartridge (14) is being accommodated in the cartridge accommodation room (24).

According to the fifth invention, since the fragrance source cartridge is pushed in the insertion direction by the cover, it is possible to make the air supply port and the air inlet adhere more strongly.

A sixth invention is according to any one of the first to fifth inventions, wherein the emission port is formed in a plural number in a center portion at the front side of the housing, and each of the air discharge port is communicated with corresponding one of the emission ports via an individual communication hole.

In the sixth invention, a plurality of emission ports (16) are formed in the center portion at the front side of the housing (20, 34). Each of the emission ports is communicated via an individual communication hole (42) with the air discharge port (50) of corresponding one of the cartridge accommodation rooms (24). That is, the fragrance that is discharged from an individual fragrance outlet (88) of the fragrance source cartridge (14) is emitted from an individual emission port through the individual communication hole.

According to the sixth invention, since the fragrance from each fragrance source cartridge is emitted from an individual emission port via an individual communication hole, the fragrance components of different fragrance source cartridges are not mixed with each other in the housing.

A seventh invention is according to any one of the first to sixth inventions, and further comprises an auxiliary airflow source that is provided in the housing and has a diaphragm provided with a piezoelectric device.

The seventh invention further comprises the auxiliary airflow source (76) that is provided independently on respective cartridge accommodation rooms and separately from the airflow source (26) provided in each cartridge accommodation room (24). As the auxiliary airflow source, it is possible to use the thing similar to the airflow source, that is, an airflow source that comprises the diaphragm that the piezoelectric device adheres, and when an alternating voltage is applied to the piezoelectric device, the diaphragm is vibrated, whereby airflow can be generated. The auxiliary airflow source is communicated via an auxiliary path (78) provided in the housing (20) with the emission port (16) or an auxiliary emission port (98) that is formed a position near the emission port.

When presenting a fragrance to a user by such an olfactory display (10), at the same time that the airflow source corresponding to the fragrance source cartridge (14) storing a target fragrance source (90) is operated or in a time-shared manner, the auxiliary airflow source is operated. Then, the fragrance discharged from the fragrance source cartridge is joined with an odorless air discharged from the auxiliary airflow source to be accelerated.

According to the seventh invention, since the auxiliary airflow source is provided, it is possible to accelerate the fragrance and thus to increase an emission performance of the fragrance more.

An eighth invention is a fragrance source cartridge used in the olfactory display according to any one of the first to seventh inventions, comprising: a container main body that has an outer shape conformed to an inner shape of the cartridge accommodation room, and is formed with an air inlet in a position corresponding to the air supply port and a fragrance outlet in a position corresponding to the air discharge port; and a solid-like fragrance source stored within the container main body, wherein the outer shape of the container main body has inclined surfaces inclined with respect to an insertion direction of the fragrance source cartridge.

According to the eighth invention, it is possible to provide an olfactory display with the operation and advantage similar to the first invention, capable of presenting innumerable fragrances in a range bounded in terms of time and space while retaining the miniaturization and simplicity.

Advantage of the Invention

According to the present invention, since a cartridge system that accommodates the fragrance source cartridge in the display main body attachably or detachably is adopted, it is constructed that the cartridge is used for each fragrance, and therefore, various kinds of fragrances can be presented without causing confusion of a fragrance component. Furthermore, when adopting a cartridge system, in order to make the air supply port and the air inlet adequately adhere, there are provided with slant structure in the cartridge accommodation room and the fragrance source cartridge.

That is, it becomes possible to make the air supply port and the air inlet adequately adhere with simple structure that the inclined structure is provided without providing with a complicated mechanism. Therefore, it is possible to present various kinds of fragrances within a range bounded in terms of time and space.

The above described objects and other objects, features, aspects and advantages of the present invention will become more apparent from the following detailed description of the present invention when taken in conjunction with the accompanying drawings.

BRIEF DESCRIPTION OF THE DRAWINGS

FIG. 18(A) is an illustration view showing a situation viewed form a side direction, and FIG. 18(B) is an illustration view viewed form a front direction.

FORMS FOR EMBODYING THE INVENTION

Figure 1:
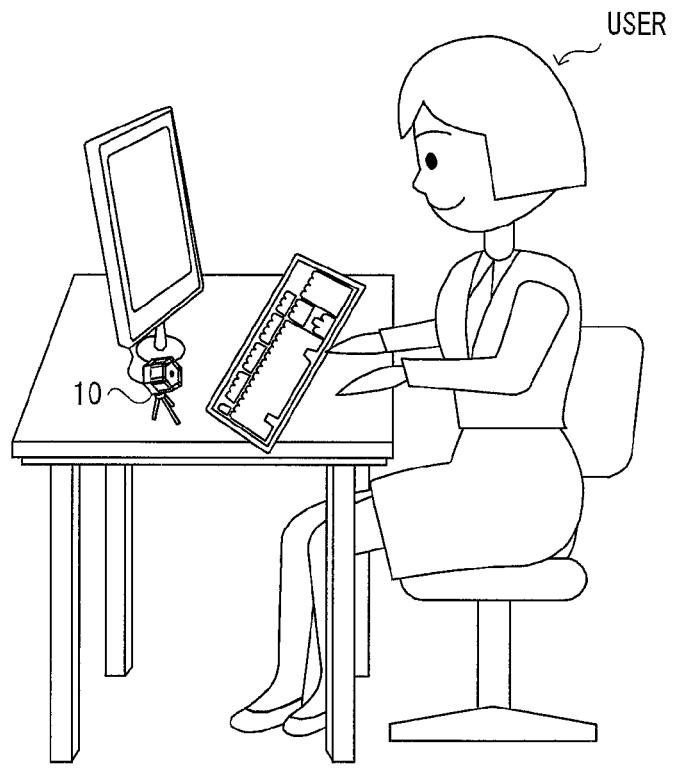
FIG. 1 is an illustration view showing a situation that a fragrance is presented to a user using an olfactory display that is an embodiment of the present invention.
Figure 2:
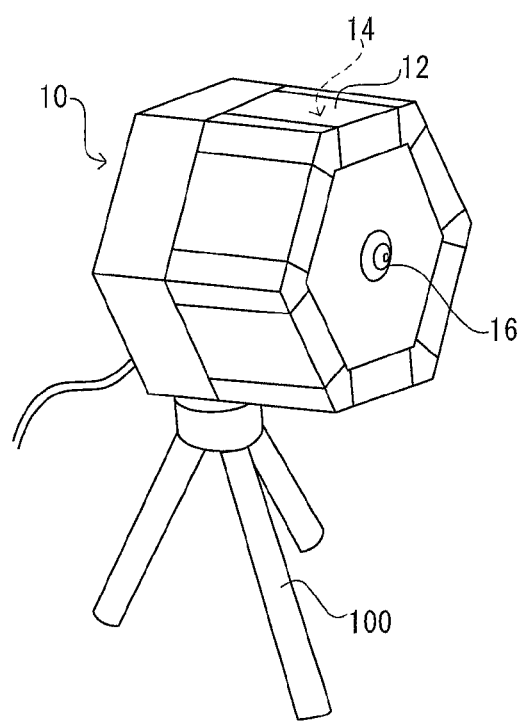
FIG. 2 is an illustration view showing a situation near the olfactory display of FIG. 1.

With referring to FIG. 1 and FIG. 2, an olfactory display 10 that is an embodiment according to the present invention is used for enhancing a reality and a presence of the content by presenting to a user the content including an image and sound to which a fragrance (olfactory information) is added. The olfactory display 10 presents a fragrance in a time-space-controllable manner, that is, within a range bounded in terms of time and space in cooperation with various kinds of audio-visual displays such as a personal computer, a television, a radio, a game machine, a karaoke machine, a camera, a DVD player, a mobile phone, etc., for example.

FIG. 1 and FIG. 2 show a situation that the olfactory display 10 is used in cooperation with a personal computer as an example. In such a case, the olfactory display 10 is attached to an LCD display 100, a keyboard or the like such that an emission port 16 that emits a fragrance is turned to a direction of a face of the user, or attached to a tripod 100 or the like to be arranged around the user.

Figure 3:
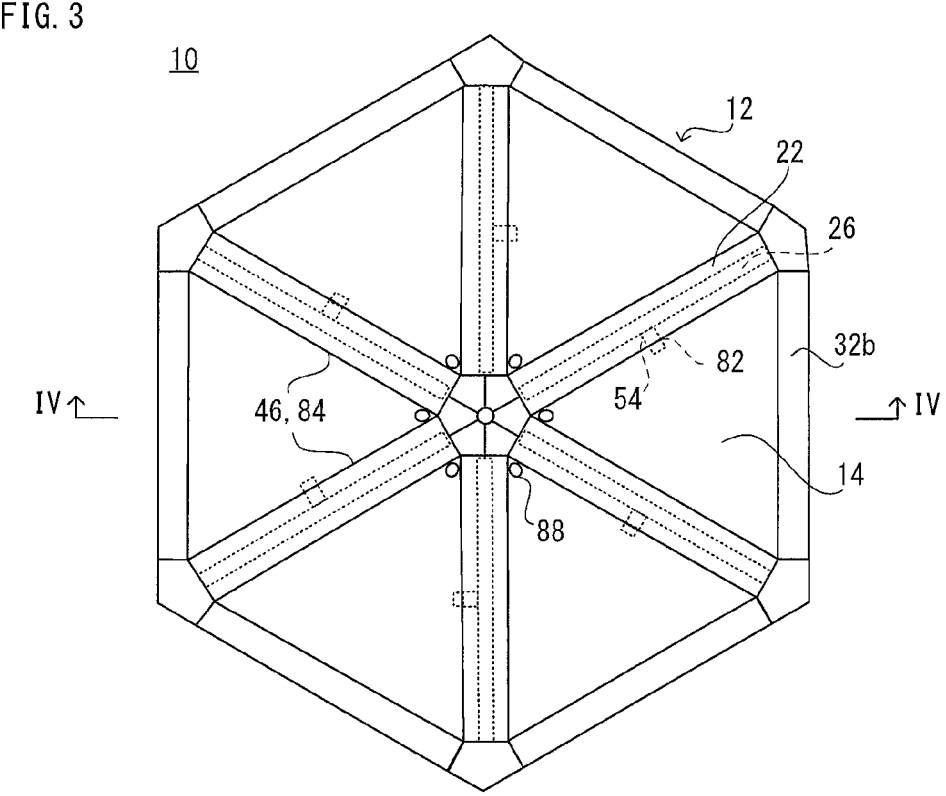
FIG. 3 is an illustration view schematically showing internal structure of the olfactory display of FIG. 1 while viewed from a front direction.
Figure 4:
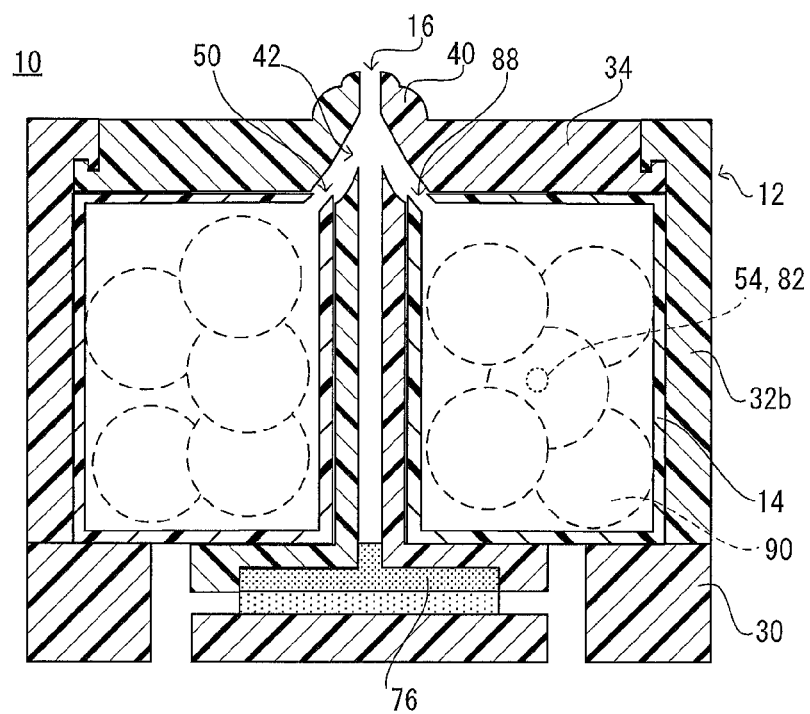
FIG. 4 is a cross-sectional view schematically showing the internal structure of the olfactory display of FIG. 1 while viewed from a side direction, showing a cross-section cut at a line IV-IV in FIG. 3.
Figure 5:
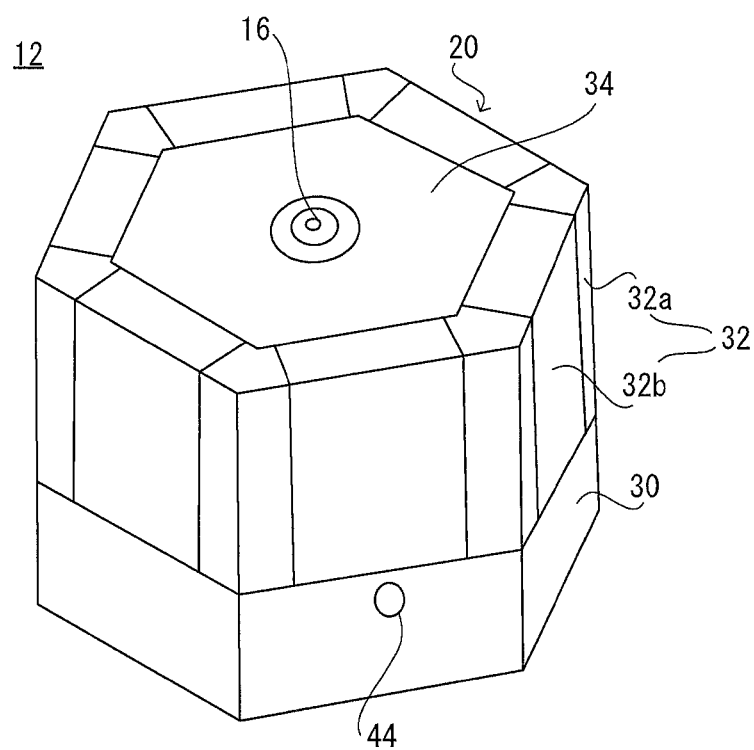
FIG. 5 is a perspective view showing an appearance of a display main body provided in the olfactory display of FIG. 1.
Figure 6:
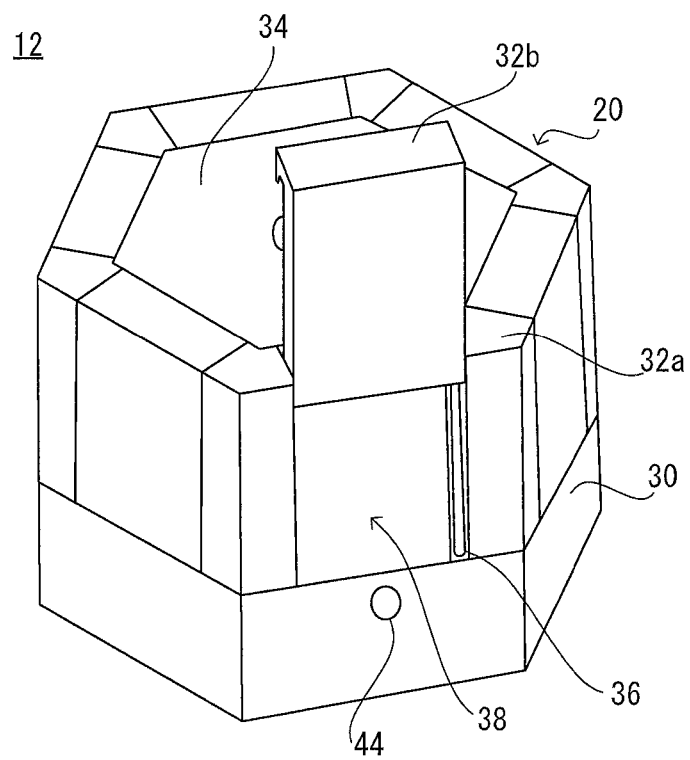
FIG. 6 is an illustration view showing a situation that a cover of the display main body of FIG. 5 is opened.
Figure 7:
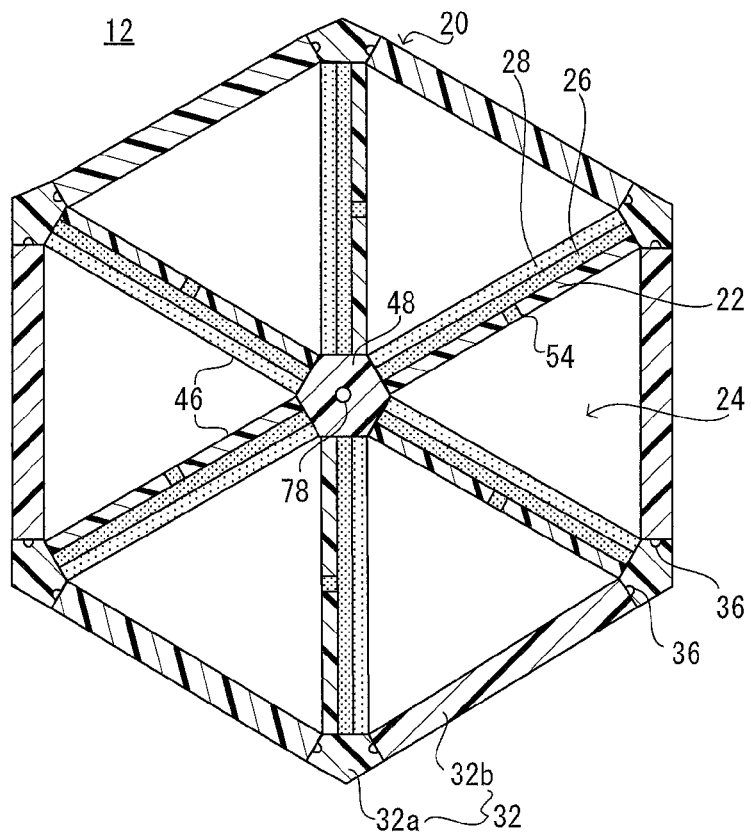
FIG. 7 is a cross-sectional view schematically showing internal structure of the display main body of FIG. 5 while viewed from a front direction.
Figure 8:
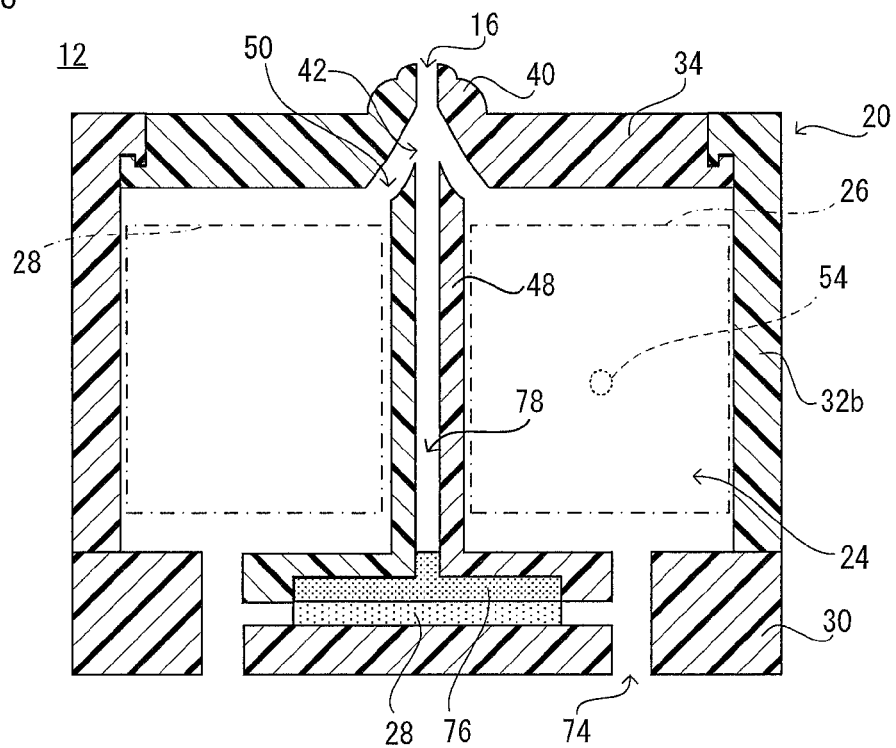
FIG. 8 is a cross-sectional view schematically showing the internal structure of the display main body of FIG. 5 while viewed from a side direction.

FIG. 3 is an illustration view schematically showing internal structure of the olfactory display 10 while viewed from a front direction, and shows a situation of the inside of the olfactory display 10 while omitting an emission plate 34 describe later. Furthermore, FIG. 4 is a cross-sectional view of the olfactory display 10 cut at a line IV-IV in FIG. 3, and schematically shows the internal structure of the olfactory display while viewed from a side direction. As shown in FIG. 3 and FIG. 4, the olfactory display 10 comprises a display main body 12 and a plurality of fragrance source cartridges 14 accommodated in its inside attachably and detachably. In this embodiment, six (6) fragrance source cartridges 14 are accommodated in the display main body 12 to be arranged in a circumferential direction. As for the number of the fragrance source cartridges 14 capable of being simultaneously accommodated in the display main body 12 (the number of cartridge accommodation rooms 24 describe later), although not limited especially, when taking the miniaturization and simplicity of an apparatus into consideration, it is preferable to set as eight (8) from four (4).

In the following, structure of the olfactory display 10 will be specifically described. As shown in FIG. 5-FIG. 8, the display main body 12 comprises a housing 20 that constitutes an outer shell and a plurality of cartridge accommodation rooms 24 that are formed by dividing an internal space of the housing 20 by partitions 22. Furthermore, there are provided in each of the cartridge accommodation rooms 24 an airflow source 26 and an operation noise suppressing portion 28 that are arranged in close contact to each other inside the partition 22.

The housing 20 includes a base portion 30, a side wall 32 and an emission plate 34, and is formed in a shape of a hollow hexagonal prism of proper materials such as an acrylic resin, a fluororesin or a stainless steel. A size of the housing 20 is 65 mm in length between opposite vertex when viewed from a front direction, and 55 mm in length of an axial direction (front-back direction).

The base portion 30 is formed in a shape of a regular hexagonal plate, and arranged in a rear side of the housing 20 (reverse to user). The side wall 32 is provided in a peripheral portion of the base portion 30. The side wall 32 is formed in a shape of a hexagonal cylinder by holders 22a each connected to each corner of the peripheral portion of the base portion 30 and slide covers 32b each provided between the holders 32a. Slide grooves 36 are formed on the side surface of the holder 32a, and projection portions (not shown) formed on side surfaces of the slide cover 32b are inserted into the slide grooves 36. Accordingly, the slide cover 32b is made slidable between the holders 32a. As described later, each of openings between the holders 32a functions as a cartridge exchange portion 38 of the cartridge accommodation room 24, and the slide cover 32b is used for opening and closing of this cartridge exchange portion 38. Furthermore, when the fragrance source cartridge 14 is accommodated in the cartridge accommodation room 24, the slide cover 32b is brought into contact to a tail end of the fragrance source cartridge 14 in an insertion direction, and plays an action that pushes the fragrance source cartridge 14 in the insertion direction.

The emission plate 34 is provided in a front end portion of the side wall 32, i.e., in a front side of the housing 20. The emission plate 34 is formed in a shape of a regular hexagonal plate, and covers an end opening of the side wall 32. A projection portion 40 of a dome shape is provided in a center portion of the emission plate 34, and a communicating hole 42 that is extended in a thickness direction of the emission plate 34 is formed so as to penetrate the center portion of this projection portion 40. This communicating hole 42 has a diameter reduction portion of a taper shape that diameter-reduced as it goes to the front side, and is formed in a shape of straight pipe in its front portion. A tip opening of the projection portion 40 functions as an emission port 16, and the communicating hole 42 makes the emission port 16 and each of the cartridge accommodation rooms 24 communicate to each other. A diameter of the emission port 16 is 1.0 mm, for example, and a thickness of the emission plate 34 including the projection portion 40 is 12 mm, for example.

Furthermore, a screw hole 44 for attaching the tripod 100 is formed in a proper position of the housing 20. The screw hole 44 is formed on a side surface of the base portion 30 in this embodiment. Furthermore, the standard of the screw hole 44 should suit the tripod for cameras. Since the standard of the screw of the tripod for cameras is unified by the global standard, if the standard of the screw hole 44 is fitted to the standard, it is possible to use the tripod for the cameras around the world as the tripod 100 for the olfactory display 10 with no change, and thus, it is convenient.

Furthermore, the internal space of the housing 20 is divided by the radial partitions 22 that couple opposite holders 32b, and six (6) cartridge accommodation rooms 24 each having a shape of equilateral triangular prism and arranged in a circumferential direction are formed in the housing 12. That is, an inner surface of the cartridge accommodation room 24 have two (2) inclined surfaces 46 that converge toward the center of the housing 20, i.e., that are inclined inwardly with respect to an insertion direction of the fragrance source cartridge 14 describe later. Furthermore, a center axis 48 that is a coupling portion of each partition 22 is formed in a shape of a hexagonal prism, and projected from the base portion 30 such that a tip end portion is extended in the communicating hole 42. The tip end portion of the center axis 48 is formed as a tapered shape that notches of a shape of groove are formed on outer periphery surface, and functions as a guide portion that guides a fragrance discharged from a fragrance outlet 88 of the fragrance source cartridge 14 describe later in a direction of the emission port 16. Accordingly, a back flow of the fragrance and permeation of the fragrance into other fragrance source cartridges 14 can be prevented.

An air discharge port 50 that is communicated with the emission port 16 via the communicating hole 42 formed in the emission plate 34 is formed in each of the cartridge accommodation rooms 24. Furthermore, the cartridge exchange portion 38 that can be opened and closed by the slide cover 32b is formed in each of the cartridge accommodation rooms 24.

Furthermore, the airflow source 26 is provided in each of the cartridge accommodation rooms 24 to be closely contacted to the partition 22. This airflow source 26 is arranged in the partition 22, i.e., radially arranged in the housing 20, and constitutes a part of the partition 22. A nozzle 52 that is provided in a center portion of the airflow source 26 is communicated with the inside of the cartridge accommodation room 24, and functions as an air supply port 54 that makes an air flow into the fragrance source cartridge 14 that is accommodated in the cartridge accommodation room 24. A size of the airflow source 26 is in 20 mm long, 20 mm wide, and 2 mm thickness, for example. Furthermore, a diameter of the air supply port 54 (inner diameter of the nozzle 52) is 1.0 mm, for example.

Figure 9:
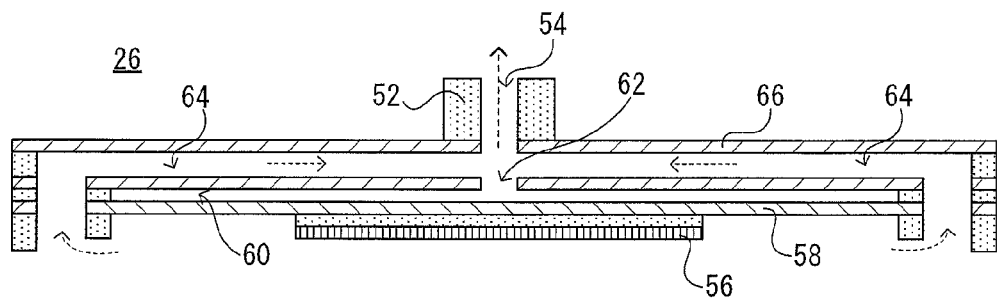
FIG. 9 is a cross-sectional view showing a cross-section when an airflow source provided on the display main body of FIG. 5 is cut in a direction of a diagonal line.

FIG. 9 shows a cross-section when the airflow source 26 is cut in a direction of a diagonal line. The airflow source 26 is of a piezoelectric system, and provided with a diaphragm 58 that a piezoelectric device (piezoelectric element) 56 adheres, and by applying an alternating voltage (sign wave voltage or rectangular wave voltage) to the piezoelectric device 56, the diaphragm 58 is bent and vibrated in a thickness direction thereof to generate an airflow.

In the following, an operation of the airflow source 26 will be briefly described. In the airflow source 26, according to the vibration of approximately 26 kHz of the diaphragm 58 that a disc-like piezoelectric device 56 adheres, suction and discharge of the air to and from an air hole 62 formed in a center portion of a pump room 60 are repeated. The air taken into the pump room 60 from a suction passage 64 at the time of suction passes at the time of discharge through the nozzle 52 that is arranged coaxially with the air hole 62 on a top plate 66, and expanded in a tapered conduit in the nozzle 66 to be discharged. At this time, since a negative pressure portion occurs in a space between the air hole 62 and the nozzle 52 due to a Venturi effect, the air in the suction passage 62 is continuously sucked. Accordingly, a continuous pump operation toward the nozzle 52 from the suction passage 62 can be obtained.

The airflow source (airflow source of the piezoelectric system) 26 thus driven by the piezoelectric device 56 does not have a rotation mechanism such as a blower fan or a scroll blower, and thus, can be reduced in a size and a height, and further consumption electricity is also small. In addition, such the airflow source is of no vibration essentially and has a feature that a higher static pressure can be produced within a short time period. For such an airflow source 26, a micro blower (type number: MZBX001) manufactured by Murata Manufacturing Co., Ltd, for example, is available.

Returning to FIG. 7, in the rear side of the airflow source 26 (an upstream side of the air passage), the operation noise suppressing portion 28 for suppressing a leakage of an operation noise of the airflow source 16 (a vibration noise of the diaphragm 58) to the outside is provided. This operation noise suppressing portion 28 also constitutes a part of the partition 22. The operation noise suppressing portion 28 is made of suitable materials such as an acrylic resin, a fluororesin, a stainless steel, etc., and formed with a cavity portion in the rear side of the diaphragm 58. A size of the operation noise suppressing portion 28 is in 20 mm long, 20 mm wide, and 2 mm thickness, for example. In addition, an open air inlet 70 of the operation noise suppressing portion 28 is communicated with the outside of the housing 20 via an air suction port 74 formed in the periphery portion of the base portion 30.

Figure 10:
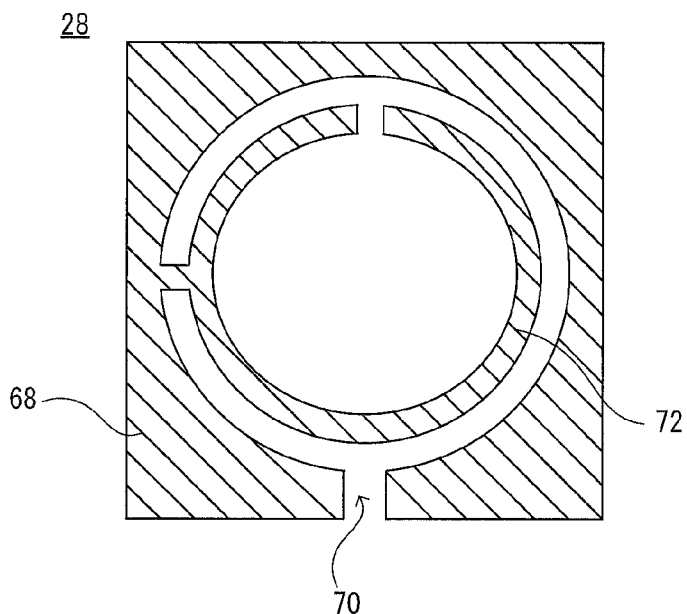
FIG. 10 is a cross-sectional view showing a cross-section when an operation noise suppressing portion provided on the display main body of FIG. 5 is cut in a direction intersecting a thickness direction perpendicularly.

FIG. 10 shows a cross-section when the operation noise suppressing portion 28 is cut in a direction intersecting a thickness direction perpendicularly. As shown in FIG. 10, the open air inlet 70 for sucking-in an air at the time that the airflow source 26 is operated is formed on a side wall 68 of the operation noise suppressing portion 28, and the inside of the operation noise suppressing portion 28 is partitioned by a C-letter shaped partitioning wall 72. Accordingly, since the operation noise of the airflow source 26 reaches the open air inlet 70 with making a detour through a maze-like air passage, the leakage of the operation noise from the open air inlet 70 can be suppressed. By providing such an operation noise suppressing portion 28, it is possible to present the fragrance to the user without giving to the user an uncomfortable feeling due to the operation noise. It is to be noted that the internal structure of the operation noise suppressing portion 28 is not restricted to a manner shown in FIG. 10. For example, the operation noise suppressing portion 28 may be a mere cavity with no partitioning wall 72 or may be provided with a partitioning wall having another shape.

Furthermore, returning to FIG. 7 and FIG. 8, an auxiliary airflow source 76 is provided in the base portion 30. The auxiliary airflow source 76 is provided independently of each cartridge accommodation room 24, and is used for acceleration of a fragrance, concentration adjustment of a fragrance component, deodorization, etc. It is preferable that the thing similar to the airflow source 26, that is, the thing that comprises a diaphragm that a piezoelectric device adheres and generates airflow by vibrating the diaphragm at a high speed when a high frequency alternating voltage is applied to the piezoelectric device is used as the auxiliary airflow source 76. The operation noise suppressing portion 28 is properly provided also in the rear side of this auxiliary airflow source 76.

Furthermore, within the center axis 48, there is formed with an auxiliary path 78 that becomes a passage of an air (odorless air) discharged from a nozzle of the auxiliary airflow source 76. The auxiliary path 78 is a penetrating hole that communicates the nozzle of the auxiliary airflow source 76 and the communicating hole 42 with each other in a straight line manner, and extended up to the emission port 16 via the communicating hole 42. A diameter of the auxiliary path 78 is 1.0 mm, for example. If the auxiliary airflow source 76 is operated, an odorless air is discharged from the nozzle of the auxiliary airflow source 76 into the auxiliary path 64. The odorless air flows straight up to the emission port 16 without moving forward a complex path and accordingly, the odorless air is emitted from the emission port 16 without generating a drop of the pressure.

Figure 11:
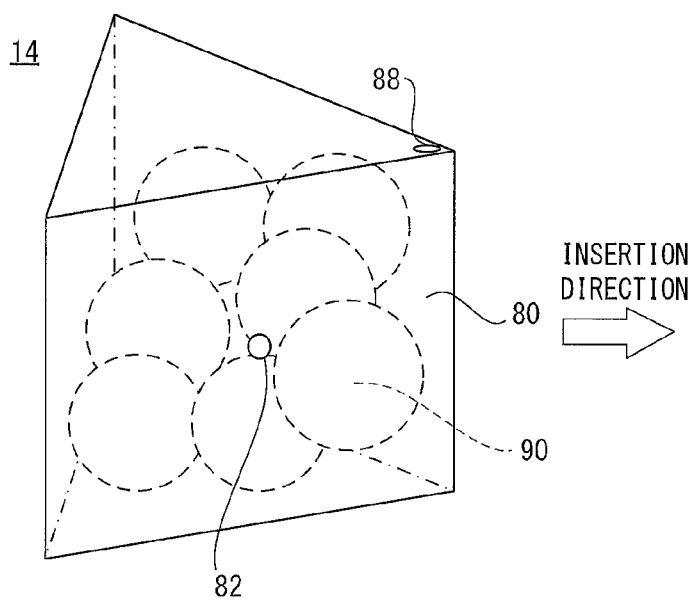
FIG. 11 is a perspective view showing an appearance of a fragrance source cartridge used for the olfactory display of FIG. 1.
Figure 12:
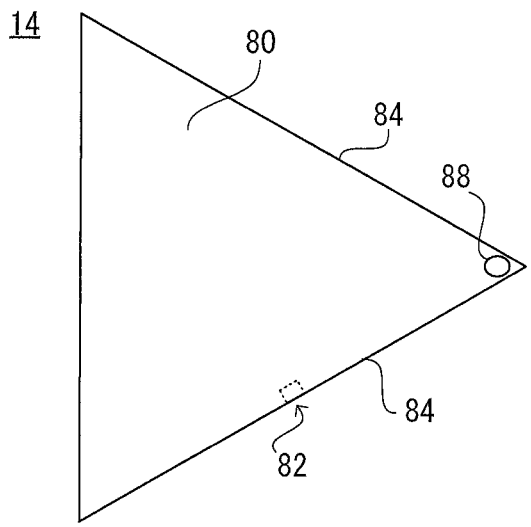
FIG. 12 is an illustration view showing an appearance of the fragrance source cartridge of FIG. 11 while viewed from a front direction.

In the cartridge accommodation room 24 of such a display main body 12, the fragrance source cartridge 14 is stored attachably or detachably. As shown in FIG. 11 and FIG. 12, the fragrance source cartridge 14 comprises a container main body 80 formed of synthetic resin such as polyethylene or polypropylene, etc. The container main body 80 is formed in a shape of a hollow equilateral triangular prism so as to have an outer surface that meets an inner shape of the cartridge accommodation room 24 with no gap. The container main body 80 is formed with an open air inlet 82 (see FIG. 4) in a position opposite to the air supply port 54 of the cartridge accommodation room 24 when the fragrance source cartridge 14 is accommodated in the cartridge accommodation room 24. That is, an outer surface of the container main body 80 has two inclined surfaces 84 that converge in the insertion direction of the fragrance source cartridge 14, and the open air inlet 82 is formed on one inclined surface 84. A diameter of the open air inlet 82 is 1.0 mm, for example.

Furthermore, the container main body 80 is formed with a fragrance outlet 88 (see FIG. 3 and FIG. 4) in a position opposite to the air discharge port 50 of the cartridge accommodation room 24. A diameter of the fragrance outlet 88 is 1.0 mm, for example. Since each of the fragrance outlets 88 is communicated with the emission port 16 in approximately a straight line manner via the communicating hole 42, the fragrance that is discharged from the fragrance outlet 88 is emitted from the emission port 16 without reducing a force. Furthermore, since an internal path that the fragrance discharged from the fragrance source cartridge 14 in the display main body 12 is brought into contact to is only the communicating hole 42 of the emission plate 34, adhesion of the fragrance component to the display main body 12 hardly occurs. In addition, since the diameter of each of the open air inlet 82 and the fragrance outlet 88 is small, when not operating the of airflow source 26, the leakage of fragrance from the fragrance source cartridge 14 hardly occurs.

A solid-like fragrance source 90 is stored in the inside of the container main body 80. The solid-like fragrance source 90 is manufactured by soaking (impregnating) liquid aromatic material into granular porous material, and by holding the liquid aromatic material on an outer surface and within pores of the porous material. For the aromatic material, natural aromatic materials, synthetic aromatic materials and compound aromatic materials thereof are available appropriately. For the porous material, a granular body such as calcium silicate, silica gel, rock wool, diatomaceous earth, zeolite, peat, charcoal, vermiculite, bentonite, perlite, carbon nanotube, active carbons, etc. are available appropriately. A particle size and shape of the porous material is not restricted especially, but, if a passage resistance, etc. within the container main body 80 are taken into account, it is preferable that the particle size is around 1-6 mm and the shape is a globoid. In this embodiment, fifteen (15) fragrance sources 90 that the liquid aromatic material is soaked into the globoid of the calcium silicate having an average particle size of 4 mm are enclosed in the container main body 80 of each fragrance source cartridge 14. By thus using the solid-like fragrance source 90, it is possible to gradually release the aromatic material (fragrance component) from the fragrance source 90. That is, since the fragrance source 90 can continuously release the fragrance component therefrom for a long period of time, it is possible to prolong a life (available period) of the fragrance source cartridge 14.

Figure 13:
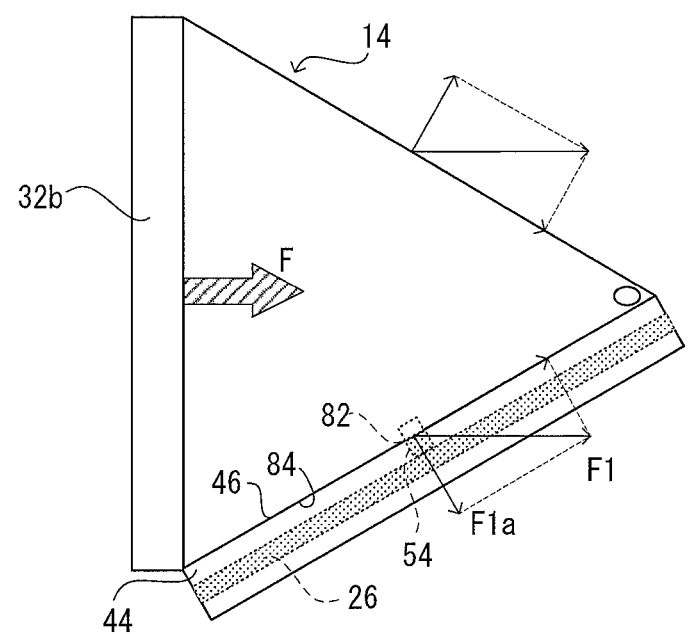
FIG. 13 is an illustration view for describing a stress acting on the fragrance source cartridge in the olfactory display of FIG. 1.

When the fragrance source cartridge 14 is accommodated in the cartridge accommodation room 24 of the display main body 12, by rendering the slide cover 32b in an opened state and pushing the fragrance source cartridge 14 toward the center axis 48 from the cartridge exchange portion 38, the fragrance source cartridge 14 is accommodated in the cartridge accommodation room 24. Then, by rendering the slide cover 32b in a closed state, the tail end of the fragrance source cartridge 14 (container main body 80) in the insertion direction can be held. At this time, since the cartridge accommodation room 24 has inclined surfaces 46 inclined inwardly with respect to the insertion direction as shown in FIG. 13, a force F that the slide cover 32b pushes the fragrance source cartridge 14 in the insertion direction is received by the inclined surfaces 46 of the cartridge accommodation room 24. A force F1 acting on the inclined surface 46 of this cartridge accommodation room 24 has a vector component F1a perpendicular to the inclined surface 46. That is, since the force F1a that presses the inclined surface 84 of the fragrance source cartridge 14 to the inclined surface 46 of the cartridge accommodation room 24 acts, adhesiveness of a coupling portion of the air supply port 54 of the display main body 12 and the open air inlet 82 of the fragrance source cartridge 14 increases, and thus, the both are made to adhere appropriately.

Furthermore, since the cartridge accommodation room 24 and the fragrance source cartridge 14 have the inclined surfaces 46 and 84 inclined inwardly in the insertion direction, an entrance portion (that is, cartridge exchange portion 38) of the cartridge accommodation room 24 becomes larger than a portion in the front side in the insertion direction of the fragrance source cartridge 14. Therefore, it is easy to insert the fragrance source cartridge 14 into the cartridge accommodation room 24.

As described above, the olfactory display 10 having such the structure presents to the user a content presented by a personal computer or the like and includes an image and sound by adding a fragrance to the content. For example, in accordance with a scene change of a video content, a fragrance of vanilla can be emitted in a scene that a vanilla ice cream is eaten, and a fragrance of the sea can be emitted in a scene of the beach.

Specifically, a controller (not shown) of the olfactory display 10 applies, according to an instruction signal sent from a personal computer or the like, an alternating voltage (frequency of 26 kHz, 19.5 Vp-p, for example) to the piezoelectric device 56 of the airflow source 26 corresponding to the fragrance source cartridge 14 that is stored with the target fragrance source 90. Then, the diaphragm 58 is bent and vibrated at a high speed, and therefore, the air is sucked from the open air inlet 74, and a high speed and high-pressure air is sent into the fragrance source cartridge 14 via the open air inlet 82 from the nozzle 52 (air supply port 54) of the airflow source 26. A gas-like fragrance component volatilized from the fragrance source 90 is included in the air in the fragrance source cartridge 14, and the air that includes the fragrance component is discharged into the communicating hole 42 from the fragrance outlet 88. Furthermore, the controller of the olfactory display 10 operates the auxiliary airflow source 76 at the same time that the airflow source 26 provided in the fragrance source cartridge 14 that stores a target fragrance source 90 is operated or in a time-shared manner. The odorless air discharged from the nozzle of the auxiliary airflow source 76 goes direct to the emission port 16 through the inside of the auxiliary path 78 like a straight line. The fragrance discharged from the fragrance outlet 88 joins with the odorless air discharged from the auxiliary airflow source 76 within the communicating hole 42 to be accelerated, and vigorously emitted from the emission port 16 without most time delay to the instruction signal from the personal computer. Then, when the application of the alternating voltage to the piezoelectric device 56 is stopped, the emission of the fragrance from the emission port 22 is also stopped.

At this time, since the piezoelectric type airflow source 26 is used, the start and stop of the emission of the fragrance is performed with excellent responsiveness (that is, a precise temporal control is possible), and further, the presentation of a continuous and constant fragrance not being pulsatile is also possible. Furthermore, since the coupling portion of the air supply port 54 of the display main body 12 and the open air inlet 82 of the fragrance source cartridge 14 adhere appropriately, the air leakage in this coupling portion hardly occurs, but a high static pressure can be generated in the fragrance source cartridge 14 in a short time by utilizing the capability of the airflow source 26 to the utmost. Furthermore, since the fragrance outlet 88 of the fragrance source cartridge 14 and the emission port 16 of the display main body 12 are communicated with each other almost linearly and thus a distance (the length of the communicating hole 42) from the fragrance outlet 88 to the emission port 16 is also short, the fragrance discharged from the fragrance outlet 88 goes to the emission port 16 without reducing the force. Furthermore, since the communicating hole 42 has the diameter reduction portion, a speed of the fragrance that passes the communicating hole 42 is accelerated by the Venturi effect. Therefore, the fragrance is vigorously emitted from the emission port 16 with directivity, and therefore, it is possible to present the fragrance to a range restricted very much spatially (that is, only near a face of the user). Furthermore, adhesion (lingering fragrance) of the fragrance component in the communicating hole 42 is also prevented.

Furthermore, since the auxiliary airflow source 76 is provided, the fragrance can be accelerated and an emission performance of the fragrance is improved more. Furthermore, the concentration control of the fragrance component becomes to be performed by changing the drive rate of the airflow source 26 and the auxiliary airflow source 76 to adjust the mixed rate of the fragrance from the fragrance source cartridge 14 and the odorless air form the auxiliary airflow source 76. Furthermore, if the fragrance component that is presented is sublimated or diluted by continuously operating the auxiliary airflow source 76 to emit only the odorless air after operating the airflow source 26 to present the fragrance, quicker deodorization can be performed as compared with free diffusion of the fragrance component as it is.

Furthermore, in this embodiment, six (6) cartridge accommodation rooms 24 are provided, and the fragrance is emitted from a single emission port 16 via the communicating hole 42. Therefore, it is, of course, possible to present six (6) kinds of fragrances individually, and by making the airflow sources 26 of respective cartridge accommodation rooms 24 operate simultaneously or a time-shared manner, the fragrances can be presented while being mixed. On the assumption that the fragrance sources 90 of the fragrance source cartridges 14 accommodated in the cartridge accommodation rooms 24 are A, B, C, D, E and F, for example, a number of kinds of the fragrance can be presented by mixing the fragrances such as "A+B, A+C, - - - , E+F, - - - , B+C+D−E+F, A+B+C+D+E+F". Furthermore, by adjusting a Duty ratio of an input signal of each airflow source 26 etc., it is possible to change suitably the rate that the fragrances are mixed.

Since the fragrance source 90 is stored in the fragrance source cartridge 14 and this fragrance source cartridge 14 is accommodated in the cartridge accommodation room 24 attachably and detachably, it is constructed that the fragrance source cartridge 14 is used for corresponding to the fragrance source 90, and therefore, the fragrance component does not adhere to the inner wall surface of the cartridge accommodation room 24. Therefore, even if the fragrance source cartridge 14 is exchanged, a fragrance component is not mixed up, and it becomes possible to present a number of kinds of fragrances appropriately by exchanging the fragrance source cartridge 14. Furthermore, since the airflow source 26 is arranged radially, the cartridge exchange portion 38 can be formed on the side wall 32 of the housing 20. Therefore, as compared with a case where the cartridge exchange portion 38 is formed on the front wall (emission plate 34) or rear wall (base portion 30) of the housing 20, it becomes easy to provide a cover in each cartridge exchange portion 38 individually and thus the individual exchange of the fragrance source cartridge 14 becomes simple.

According to this embodiment, since the cartridge system that accommodates the fragrance source cartridge 14 to the cartridge accommodation room 24 of the display main body 12 attachably and detachably is adopted, it is possible to present numerous fragrances appropriately without producing confusion of a fragrance component. Furthermore, when adopting the cartridge system, the inner surface of the cartridge accommodation room 24 and the outer surface of the fragrance source cartridge 14 (container main body 80) are formed with the inclined surfaces inclined with respect to the insertion direction of the fragrance source cartridge 14, and therefore, the coupling portion of the air supply port 54 of the display main body 12 and the open air inlet 82 of the fragrance source cartridge 14 can be made adhere appropriately. That is, by closely contacting the air supply port 54 and the open air inlet 82 with each other by simple structure that the inclined surfaces are provided on the cartridge accommodation room 24 and the fragrance source cartridge 12 without using a complicated mechanism (biasing means such as a flat spring), a high static pressure can be generated in the fragrance source cartridge 14 in a short time by utilizing the capability of the airflow source 26 to the utmost. Therefore, according to this embodiment, it is possible to present numerous fragrances within a range bounded in terms of time and space, while retaining the miniaturization and simplicity.

In addition, in the above-mentioned embodiment, when the fragrance source cartridge 14 is accommodated in the cartridge accommodation room 24, the coupling portion of the air supply port 54 and the open air inlet 82 is made to adhere more strongly by pushing the tail end of the fragrance source cartridge 14 in the insertion direction with the slide cover 32b. However, it is not necessary to necessarily push the fragrance source cartridge 14 by the slide cover 32b. The fragrance source cartridge 14 is formed of comparatively elastic materials such as polypropylene or polyethylene. Therefore, since the cartridge accommodation room 24 and the fragrance source cartridge 14 have the inclined surfaces 46 and 84 inclined inwardly in the insertion direction, when the fragrance source cartridge 14 is pushed into the cartridge accommodation room 24, it is rendered in a state where the fragrance source cartridge 14 is fit to the cartridge accommodation room 24. Accordingly, since the force (force in the insertion direction) of the time that the fragrance source cartridge 14 is pushed into the cartridge accommodation room 24 is kept, the force that presses the inclined surfaces 84 of the fragrance source cartridge 14 to the inclined surfaces 46 of the cartridge accommodation room 24 acts, and therefore, the coupling portion of the air supply port 54 and the open air inlet 82 adhere adequately. This is the same about other embodiments describe later.

Furthermore, in order to improve more the adhesiveness of the coupling portion of the air supply port 54 of the display main body 12 and the open air inlet 82 of the fragrance source cartridge 14, an elastic material layer (not shown) formed of elastic material with high pliability such as silicone rubber may be laminated to the outer surface of the container main body 80 or the inner surface of the cartridge accommodation room 24. For example, an elastic material layer may be laminated to each of the two inclined surfaces 84 of the container main body 80, and an elastic material layer may be formed to the outer surface that the open air inlet 82 of the container main body 80 is formed.

Figure 14:
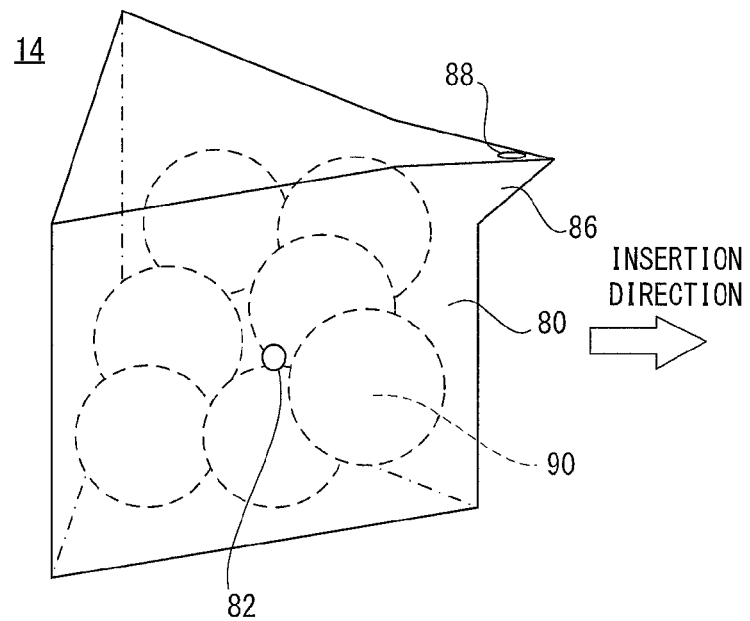
FIG. 14 is a perspective view showing an appearance of another example of a fragrance source cartridge used for the olfactory display of FIG. 1.

Furthermore, as shown in FIG. 14, a projection portion 86 may be formed on the container main body 80 of the fragrance source cartridge 14. Specifically, the projection portion 86 is formed in a shape of a beak (a shape of a triangular pyramid), and projects toward the center axis 48 from the front end of the container main body 80. Then, the fragrance outlet 88 is formed to this projection portion 86. By thus forming the beak-like projection portion 86 on the container main body 80, the fragrance outlet 88 becomes to be formed in a position nearer the emission port 16 (auxiliary path 78 side), and therefore, it becomes possible to make the fragrance outlet 88 and the emission port 16 communicate with each other more linearly.

Furthermore, although the olfactory display 10 is provided with the auxiliary airflow source 76 in the above-mentioned embodiment, the auxiliary airflow source 76 does not necessarily need to be provided. If not providing the auxiliary airflow source 76, it is possible to make the airflow source 26 provided in the cartridge accommodation room 24 function as an auxiliary airflow source, for example. In such a case, a non-fragrance source cartridge is prepared, and accommodated in at least one of the cartridge accommodation rooms 24. In addition, the non-fragrance source cartridge may be a cartridge that only the granular body that the fragrance component is not added, e.g. only the granular body of the porous body, non-porous body, etc. that no liquid aromatic material is soaked is stored without storing the fragrance source 90, or a cartridge that is made into a vacant room containing nothing. Then, if the airflow source 26 of the cartridge accommodation room 24 that the fragrance source 90 is not stored is operated to discharge the odorless air after presenting a fragrance by operating the airflow source 26 of the cartridge accommodation room 24 accommodated with the fragrance source cartridge 14, for example, quick deodorization is enabled. Furthermore, like a case where the fragrances are mixed, if the airflow source 26 of the cartridge accommodation room 24 accommodating the fragrance source cartridge 14 and the airflow source 26 of the cartridge accommodation room 24 that the fragrance source 90 is not accommodated are operated simultaneously on in a time-shared manner, the concentration of the fragrance component can be adjusted. Furthermore, if a deodorization cartridge that is stored with a deodorizer inside is utilized, the quicker deodorization after presentation of the fragrance becomes enabled.

When providing the auxiliary airflow source 76, although discharge performance (static pressure generation ability) of the airflow source 26 and discharge performance of the auxiliary airflow source 76 may be made comparable, the discharge performance of the auxiliary airflow source 76 may be made higher than the discharge performance of the airflow source 26. By thus making the discharge performance of the auxiliary airflow source 76 higher than the discharge performance of the airflow source 26, it is possible to lengthen a distance of fragrance presentation, that is, to carry the fragrance till a more distant place.

In order to enhance the discharge performance of the auxiliary airflow source 76, it is sufficient to use the auxiliary airflow source 76 comprising a piezoelectric device with a large diameter as compared with the airflow source 26, for example, or to use the auxiliary airflow source 76 comprising two or more stages of piezoelectric devices arranged in a multi-layered manner. Furthermore, if using the same thing as the airflow source 26 and the auxiliary airflow source 76, the discharge performance of the auxiliary airflow source 76 may be increased by enlarging the alternating voltage to be applied to the piezoelectric device of the auxiliary airflow source 76. If a specific example is given, the alternating voltage of 19.5 Vp-p may be applied to the piezoelectric device 56 of the airflow source 26, and the alternating voltage of 30.0 Vp-p may be applied to the piezoelectric device of the auxiliary airflow source 76. However, since a problem may occur in the durability of the auxiliary airflow source 76 when enlarging the alternating voltage applied to the piezoelectric device, it is preferable to refrain from the continuous drive of the auxiliary airflow source 76 for a long time and to perform the intermittent drive for about 3 seconds, for example.

Furthermore, although the cover 32b of the slide system is adopted as a cover that is provided in the cartridge exchange portion 38 and pushes the fragrance source cartridge 14 in the insertion direction in the above-mentioned embodiment, a specific manner of a cover is not limited in particular. For example, a cover of a horizontally-opened type may be adopted, or a cover that can be removed completely may be adopted.

Furthermore, although the cartridge exchange portion 38 is formed on the side wall 32 of the housing 20 and the fragrance source cartridge 14 is inserted toward the center axis 48 side from a lateral side of the housing 20 in the above-mentioned embodiment, not limited to this. It may be constructed such that the cartridge exchange port 38 is formed on the front wall or the rear wall of the housing 20, and the fragrance source cartridge 14 can be inserted from the front or the rear of the housing 20.

In the following, with reference to FIG. 15-FIG. 18, an olfactory display 10 that is of a type that the fragrance source cartridge 14 is inserted from the front of the housing 20, being another embodiment of the present invention will be described. However, about the same portions as those of the above-mentioned embodiment, the same reference numerals are used to omit or simplify description. This same also about other embodiments described later. In addition, FIG. 15 is an illustration view schematically showing the internal structure of the olfactory display 10 viewed form the front to show an internal situation of the olfactory display 10 while omitting the emission plate 34.

Figure 15:
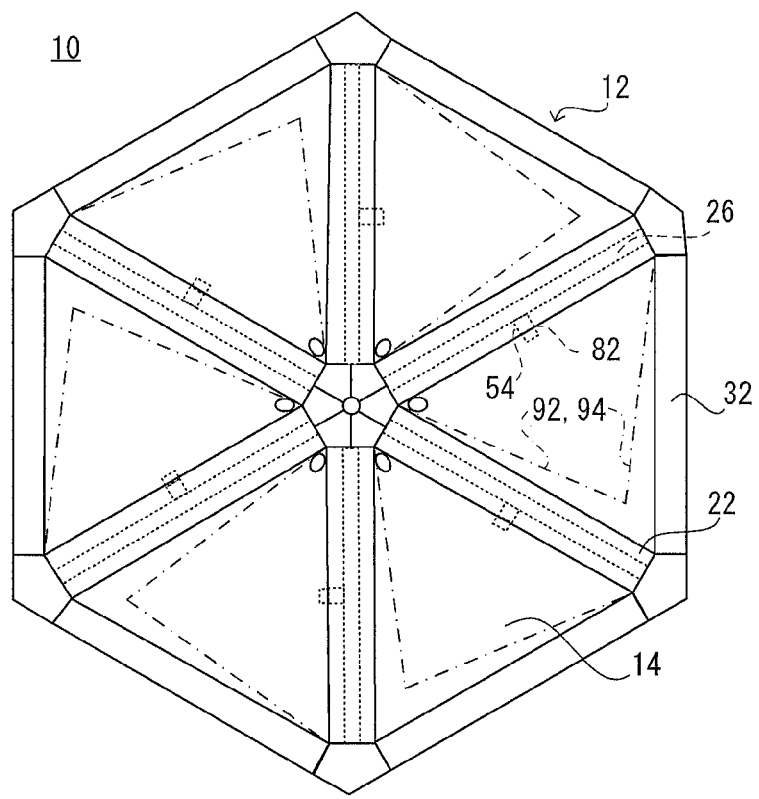
FIG. 15 is an illustration view schematically showing internal structure of an olfactory display that is another embodiment of the present invention while viewed from a front direction.

As shown in FIG. 15, in the olfactory display 10 of this embodiment, the display main body 12 comprises the housing 20 formed in a shape of a hollow hexagonal prism and six (6) cartridge accommodation rooms 24 each of a shape of approximately equilateral triangular prism formed by dividing the internal space of the housing 20 by the radial partitions 22. Furthermore, the airflow source 26 and the operation noise suppressing portion 28 are arranged within each of the partitions 22 with being closely contacted, and the air supply port 54 is formed in each of the partitions 22.

Although the housing 20 includes the base portion 30, the side wall 32 and the emission plate 34, in this embodiment, instead of the slide cover 32b provided on the side wall 32, the emission plate 34 is attached to the side wall 32 attachably or detachably. That is, the cartridge exchange portion 38 of the cartridge accommodation room 24 is formed on the emission plate 34 (front wall) side of the housing 20, and the fragrance source cartridge 14 is inserted toward the base portion 30 side from the front of the housing 20. Then, the emission plate 34 is brought into contact with the tail end of the fragrance source cartridge 14 in the insertion direction, and functions as a cover that pushes the fragrance source cartridge 14 in the insertion direction. Furthermore, in the cartridge accommodation room 24, a surface that is formed with the air supply port 54 and made to be in parallel to the insertion direction of the fragrance source cartridge 14, and remaining two surfaces are formed as inclined surfaces inclined inwardly to the insertion direction of the fragrance source cartridge 14.

Furthermore, on the olfactory display 10 of the type that the fragrance source cartridge 14 is inserted from the front, a jig (tool) insertion hole 96 (see FIG. 20 and FIG. 21) is formed on the base portion 30. The jig insertion hole 96 penetrates the base portion 30 in the front-back direction, and makes the cartridge accommodation room 24 communicate with the outside. This jig insertion hole 96 is used when removing the fragrance source cartridge 14 from the cartridge accommodation room 24. Specifically, when removing the fragrance source cartridge 14 from the cartridge accommodation room 24, after removing the emission plate 34, a stick-like jig is inserted through the jig insertion hole 96 to push the fragrance source cartridge 14 to be removed from the cartridge accommodation room 24.

Figure 16:
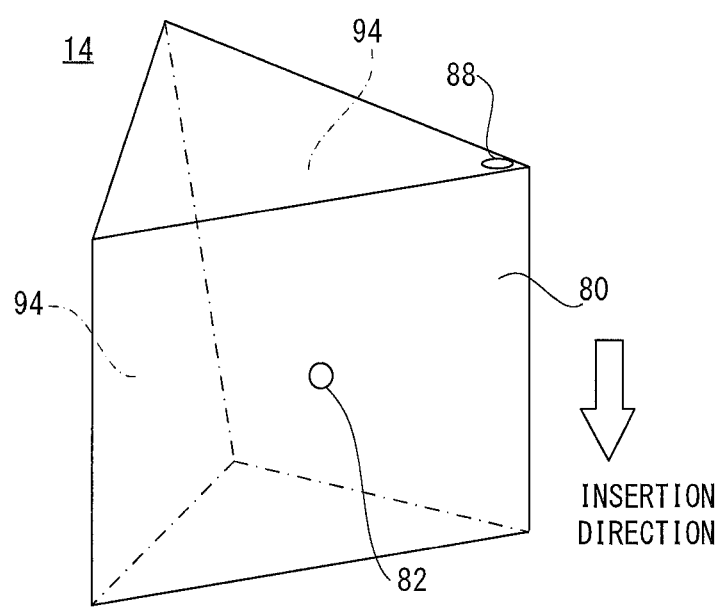
FIG. 16 is a perspective view showing an appearance of a fragrance source cartridge used for the olfactory display of FIG. 15.
Figure 17:
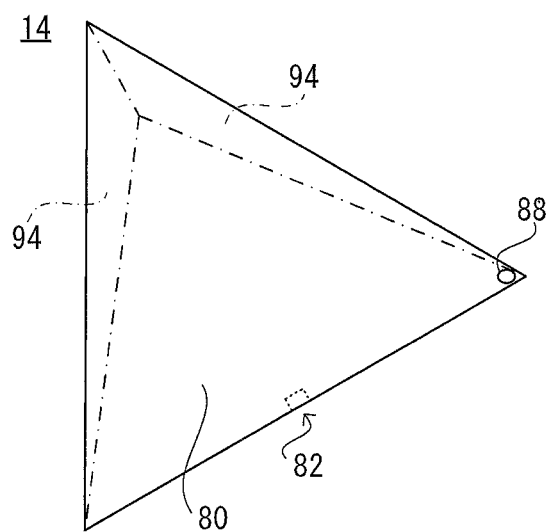
FIG. 17 is an illustration view showing an appearance of the fragrance source cartridge of FIG. 16 while viewed from a front direction.

On the other hand, the fragrance source cartridge 14 comprises the container main body 80 having an outer shape that meets an inner shape of the cartridge accommodation room 24 with no gap, as shown in FIG. 16 and FIG. 17. That is, the container main body 80 is formed in a shape of an approximately triangular prism that is reduced as goes toward the front end side in the insertion direction, wherein a surface formed with the open air inlet 82 opposite to the air supply port 54 is made to be in parallel to the insertion direction of the fragrance source cartridge 14, and the remaining two surfaces are rendered as the inclined surfaces inclined inwardly to the insertion direction of the fragrance source cartridge 14.

Figure 18:
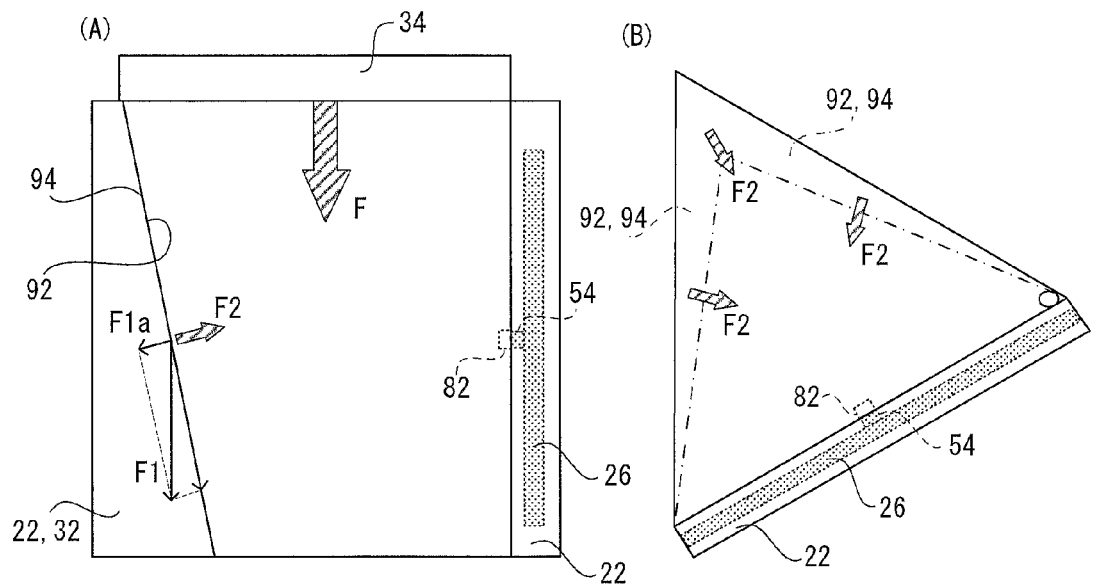
FIG. 18 is an illustration view for describing a stress acting on the fragrance source cartridge in the olfactory display of FIG. 15.

On such an olfactory display 10, when accommodating the fragrance source cartridge 14 in the cartridge accommodation room 24 of the display main body 12, the emission plate 34 is removed to make the cartridge exchange portion 38 into an opened state, and the fragrance source cartridge 14 is pushed toward the base portion 30 side from the front to accommodate into the cartridge accommodation room 24. Then, by attaching the emission plate 34, the tail end of the fragrance source cartridge 14 (container main body 80) in the insertion direction is pressed with the emission plate 34. At this time, since the cartridge accommodation room 24 has the inclined surfaces 92 inclined inwardly to the insertion direction as shown in FIG. 18, a force F that the emission plate 34 pushes the fragrance source cartridge 14 in the insertion direction is received at the inclined surfaces 92 of the cartridge accommodation room 24. Since a force F1 acting on the inclined surfaces 92 of this cartridge accommodation room 24 has a vector component F1$a$ perpendicular to the inclined surfaces 92, a counterforce F2 from the inclined surfaces 92 is generated. Since this counterforce F2 acts in a direction that the surface that is formed with the open air inlet 82 of the fragrance source cartridge 14 to the surface that is formed with the air supply port 54 of the cartridge accommodation room 24, a coupling portion of the air supply port 54 of the display main body 12 and the open air inlet 82 of the fragrance source cartridge 14 can be made to adhere appropriately.

Therefore, also in the embodiment shown in FIG. 15, similar to the embodiment shown in FIG. 3, it is possible to present numerous fragrances within a range bounded in terms of time and space, while retaining the miniaturization and simplicity.

In addition, although the two surfaces of the inner surfaces of the cartridge accommodation room 24 are made as the inclined surfaces 92 in the embodiment shown in FIG. 15, not limited to this. For example, it is sufficient all the inner surfaces are made inclined surfaces 92 inclined inwardly with respect to the insertion direction of the cartridge accommodation room 24. Furthermore, only one of the inner surfaces may be made the inclined surface 92 inclined inwardly to the insertion direction of the cartridge accommodation room 24. However, the inclined surface 92 is to be constructed that the force that pushes the fragrance source cartridge 14 into the cartridge accommodation room 24 acts in a direction that the open air inlet 82 is pressed to the air supply port 54 side.

Figure 19:
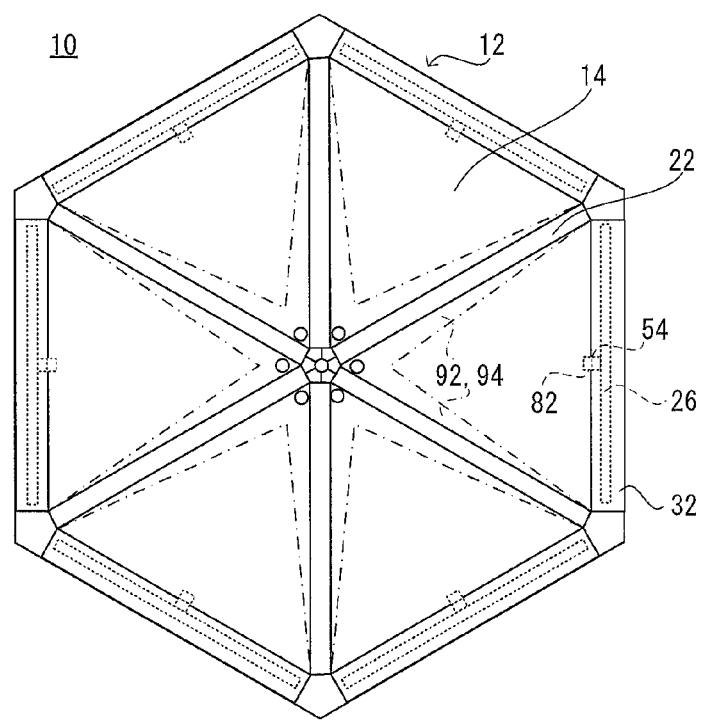
FIG. 19 is an illustration view schematically showing internal structure of an olfactory display that is a further embodiment of the present invention while viewed from a front direction.
Figure 20:
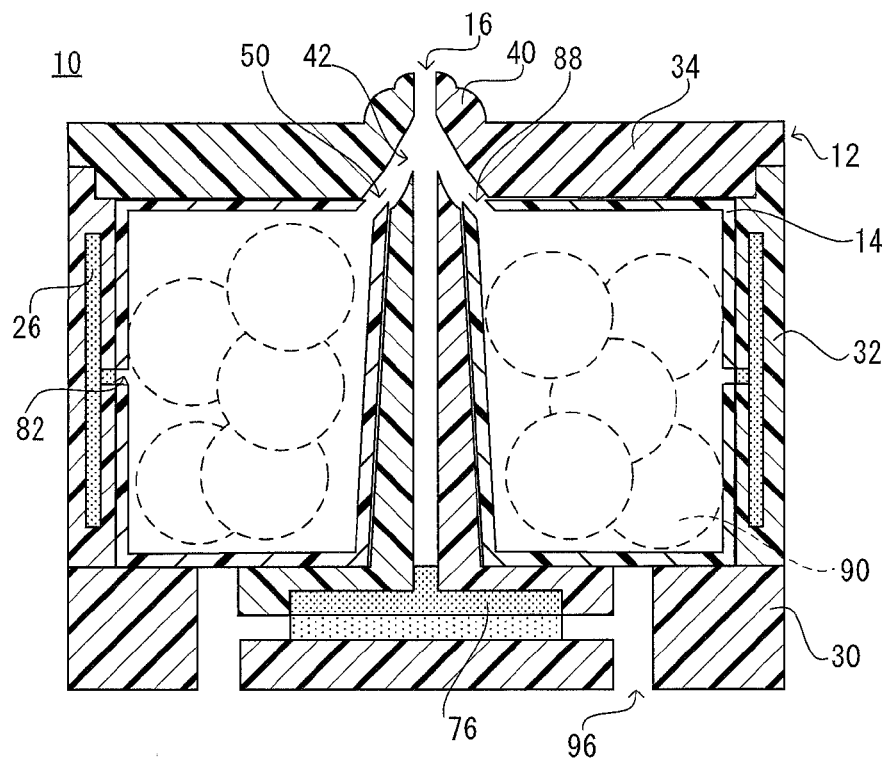
FIG. 20 is a cross-sectional view schematically showing the internal structure of the olfactory display of FIG. 19 while viewed from a side direction.

Furthermore, although the airflow source 26 is arranged within the partition 22 in each above-mentioned embodiment, not limited to this, and as shown in FIG. 19 and FIG. 20, it is possible to arrange the airflow source 26 within the side wall 32 of the housing 20 side by side in the circumferential direction.

With reference to FIG. 19 and FIG. 20, in an olfactory display 10 of this embodiment, the display main body 12 comprises the housing 20 formed in a shape of a hollow hexagonal prism and six (6) cartridge accommodation rooms 24 each of a shape of approximately equilateral triangular prism formed by dividing the internal space of the housing 20 by the radial partitions 22. Furthermore, the airflow source 26 and the operation noise suppressing portion 28 are arranged within the side wall 32, and the air supply port 54 that is communicated with each of the cartridge accommodation rooms 24. The housing 20 comprises the base portion 30, the side wall 32 and the emission plate 34, and the emission plate 34 is attached to the side wall 32 attachably or detachably. That is, the cartridge exchange portion 38 of the cartridge accommodation room 24 is formed in the emission plate 34 side of the housing 20, and the emission plate 34 functions as a cover that pushes the fragrance source cartridge 14 in the insertion direction. Furthermore, the internal surfaces of the cartridge accommodation room 24 include a surface that is formed with the air supply port 54 and made to be in parallel to the insertion direction of the fragrance source cartridge 14, and remaining two surfaces that are formed as inclined surfaces 92 inclined inwardly to the insertion direction of the fragrance source cartridge 14. On the other hand, the fragrance source cartridge 14 comprises the container main body 80 having an outer shape that meets the inner shape of the cartridge accommodation room 24, and the container main body 80 include a surface that is formed with the open air inlet 82 and made to be in parallel to the insertion direction of the fragrance source cartridge 14, and remaining two surfaces that are formed as inclined surfaces 94 inclined inwardly to the insertion direction of the fragrance source cartridge 14.

In also the embodiment shown in FIG. 19, similar to the embodiment shown in FIG. 15, a counterforce F2 from the inclined surfaces 92 acts in a direction that the surface that is formed with the open air inlet 82 of the fragrance source cartridge 14 to the surface that is formed with the air supply port 54 of the cartridge accommodation room 24, a coupling portion of the air supply port 54 of the display main body 12 and the open air inlet 82 of the fragrance source cartridge 14 can be made to adhere appropriately with increased adhesiveness. Therefore, also in the embodiment shown in FIG. 19, it is possible to present numerous fragrances within a range bounded in terms of time and space, while retaining the miniaturization and simplicity.

Furthermore, since the airflow source 26 is provided in the side wall 32 according to the embodiment shown in FIG. 19, a thickness of the partition 22 can be made small and a cross-sectional area of the center axis 48 that is a central connection portion of the partitions 22 can be made small. Accordingly, it becomes possible to form the fragrance outlet 88 in a position nearer the emission port 16 (auxiliary passage 78 side), and to make the fragrance outlet 88 and the emission port 16 communicate with each other more linearly.

In addition, in each above-mentioned embodiment, although the number of the emissions ports 16 formed in the housing 12 is one and the fragrance from each of the fragrance source cartridges 14 is emitted from the single emission port 16 through the common communicating hole 42, not limited to this. For example, as shown in FIG. 21, it is possible to provide a plurality of emission ports 16 on the housing 12.

Figure 21:
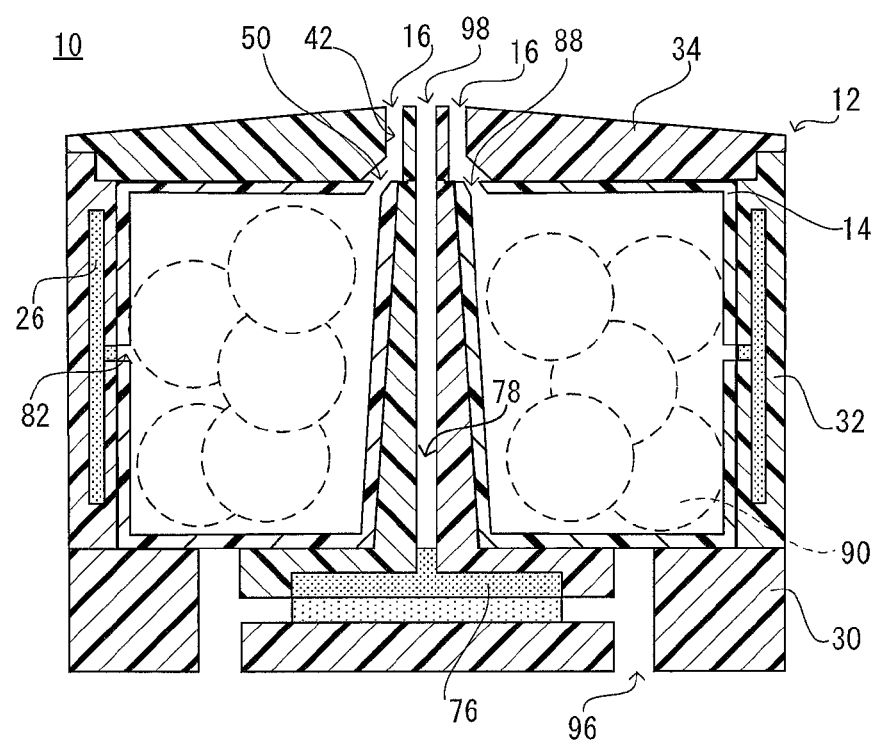
FIG. 21 is a cross-sectional view schematically showing internal structure of an olfactory display that is a still further embodiment of the present invention while viewed from a side direction.

With reference to FIG. 21, in the olfactory display 10 of this embodiment, the display main body 12 comprises the housing 20 and six (6) cartridge accommodation rooms 24 each of a shape of approximately equilateral triangular prism formed by dividing the internal space thereof by the radial partitions 22. Furthermore, the airflow source 26 and the operation noise suppressing portion 28 are arranged in the side wall 32. The housing 20 includes the base portion 30, the side wall 32 and the emission plate 34, and the emission plate 34 is attached to the side wall 32 attachably or detachably.

Figure 22:
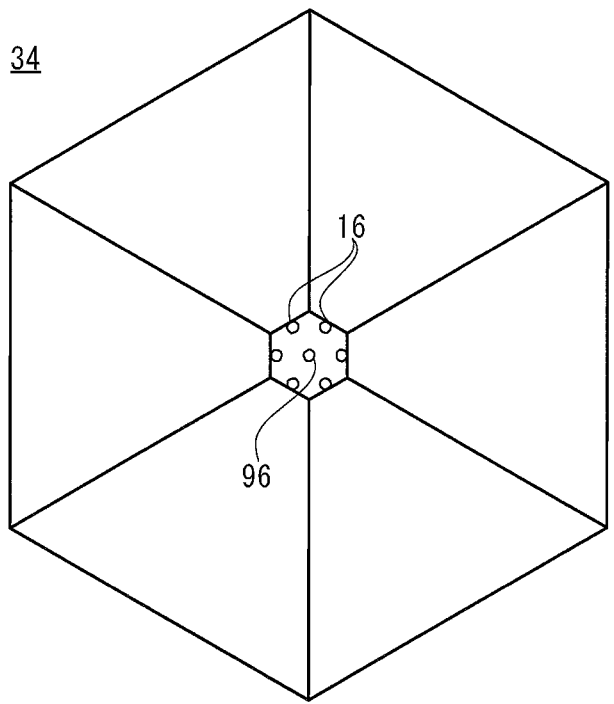
FIG. 22 is an illustration view showing an appearance of an emission plate provided on the olfactory display of FIG. 21 while viewed from a front direction.
Figure 23:
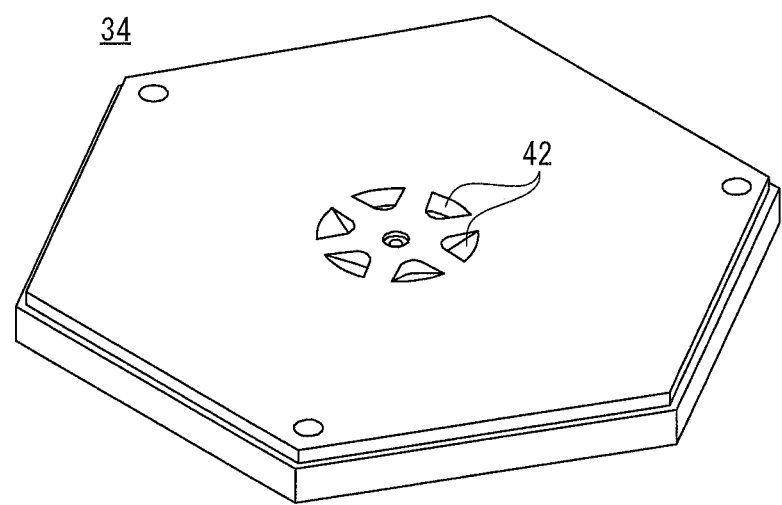
FIG. 23 is a perspective view showing a rear side of the emission plate of FIG. 22.

As shown in FIG. 22 and FIG. 23, the emission plate 34 is formed in a shape of a hexagonal plate, and the thickness thereof is thickened gradually toward the center portion from a periphery portion. In addition, a shape of the emission plate 34 can be changed suitably, and as shown in FIG. 4 etc., the projection portion 40 of a dome shape may be provided in the center portion of the emission plate 34. Six (6) emission ports 16 arranged in circular are formed in the center portion in the front side of this emission plate 34. A distance between adjacent emission ports 16 is 2 mm, for example.

Each of the emission ports 16 is communicated with the air discharge port 50 of each of the cartridge accommodation rooms 24 via individual communicating hole 42. That is, the fragrance that is discharged is emitted from the individual emission port 16 through the individual communicating hole 42 from the fragrance outlet 88 of the fragrance source cartridge 14. The fragrance entrance portion (air discharge port 50) of each communicating hole 42 is fowled slightly larger than the fragrance outlet 88 of the fragrance source cartridge 14. Then, each communicating hole 42 is diameter-reduced in a shape of a taper from the fragrance discharge port 50, and extended therefrom in a shape of a straight pipe toward the front. Accordingly, the fragrance discharged is smoothly drawn from the fragrance outlet 88 of the fragrance source cartridge 14 to the emission port 16 via the communicating hole 42.

Furthermore, an auxiliary emission port 98 is formed in the center portion of six (6) emission ports 16. That is, each emission port 16 and the auxiliary emission port 98 are collectively fanned in near positions in the center portion of the front side of the emission plate 34. The auxiliary emission port 98 is communicated with the nozzle of the auxiliary airflow source 76 via the auxiliary path 78 linearly (refer to FIG. 21).

In the embodiment shown in FIG. 21, when presenting the fragrance, at the same time that the airflow source 26 corresponding to the fragrance source cartridge 14 storing a target fragrance source 90 is operated or in a time-shared manner, the auxiliary airflow source 76 is operated. The fragrance discharged from the fragrance outlet 88 is emitted from the emission port 16, and the odorless air discharged from the auxiliary airflow source 76 is emitted from the auxiliary emission port 98. Here, since the emission port 16 and the auxiliary emission port 98 are arranged in the near positions, the fragrance from the emission port 16 and the odorless air of the auxiliary emission port 98 advance approximately the same path linearly outside the housing 20 and join outside the housing 20. Then, the fragrance from the emission port 16 is drawn by the odorless air of the auxiliary airflow source 98 to be accelerated and goes with straightness.

In also the embodiment shown in FIG. 21, similar to the embodiment shown in FIG. 15, since a coupling portion of the air supply port 54 of the display main body 12 and the open air inlet 82 of the fragrance source cartridge 14 can be made to adhere, it is possible to present numerous fragrances within a range bounded in terms of time and space, while retaining the miniaturization and simplicity. Furthermore, since the fragrance from each fragrance source cartridge 14 is emitted from an individual emission port 16, the fragrance components of different fragrance source cartridges 14 are not mixed with each other within the housing 20. In addition, although the fragrance from each fragrance source cartridge 14 is emitted from the individual emission port 16, since the emission ports 16 are arranged in the near positions, the fragrance advances approximately the same path linearly outside the housing 20. That is, also in the embodiment shown in FIG. 21, the mixing of fragrances, deodorization, etc. are possible.

Although the display main body 12 is formed in a shape of a hexagonal prism in each above-mentioned embodiment, not limited to this, but the display main body 12 may be formed in proper shape of a cube, a rectangular parallelepiped, a polygonal prism, a cylinder, etc. according to the number of the cartridge accommodation rooms 24 to be formed.

Furthermore, although a thing that the liquid aromatic material is soaked into the granular porous material is used as the solid-like fragrance source 90 in each above-mentioned embodiment, not limited to this. For example, it is possible to use as the solid-like fragrance source 9 the thing that after dissolving the base material of a solid or gelatinous at the normal temperature to the liquid aromatic material, and the liquid aromatic material is solidified or gelated by cooling at the normal temperature. However, it is preferable to use a thing that the liquid aromatic material is soaked into the porous member as the solid-like fragrance source 90 from a viewpoint that it can be manufactured simply and cheaply and that the supplement of liquid aromatic material can be performed.

Although the olfactory display 10 is installed fixedly and the fragrance is emitted only in the one direction in each above-mentioned embodiment, not limited to this, but it is possible to install the olfactory display 10 such that emission direction becomes changeable. For example, it is possible to install the olfactory display 10 on a stand that supports rotatably in a transverse direction and a lengthwise direction. In this case, it is sufficient to follow a nose of the user automatically to present the fragrance in combination with a device that detects the position of the nose of the user.

Although the fragrance is presented in conjunction to audiovisual information in each above-mentioned embodiment, the fragrance can be presented independently. For example, in vehicles such as a car, it is possible to use the olfactory display 10 as a nap prevention apparatus that detects a nap state of the driver based on a face image etc., and in response to the detection, the fragrance (pungent smell) is emitted toward to the nose of the driver. Since the olfactory display 10 can present the fragrance to a range restricted spatially very much (that is, there is directivity), it is possible to present the pungent smell only to the driver without affecting other passengers. Furthermore, different fragrance may be presented according to the temperature of the day, humidity, the weather, etc., for example.

The specific numerical values mentioned in this specification are only examples, and changeable properly in accordance with the change of product specifications.

DESCRIPTION OF NUMERALS

10—olfactory display
12—display main body
14—fragrance source cartridge
16—emission port
20—housing
22—partition
24—cartridge accommodation room
26—airflow source
28—operation noise suppressing portion
30—base portion (rear wall of housing)
32—side wall (side wall of housing)
32*b*—slide cover
34—emission plate
38—cartridge exchange portion
46, 92—inclined surfaces of cartridge accommodation room
50—air discharge port
54—air supply port
58—piezoelectric device
76—auxiliary airflow source
80—container main body
84, 94—inclined surfaces of fragrance source cartridge
86—projection portion
88—fragrance outlet
98—auxiliary emission port

The invention claimed is:

1. An olfactory display that includes a display main body and a fragrance source cartridge, and presents a fragrance within a range bounded in terms of time and space, wherein
    the display main body comprises
        a housing having an emission port in a center portion in a front side;
        a plurality of cartridge accommodation rooms that are formed by dividing an internal space of the housing by radial partitions, each of the cartridge accommodation rooms having an air supply port and an air discharge port;
        a communicating hole that is provided in the housing to make respective air discharge ports communicate with the emission port;

cartridge exchange portions each formed in each of the cartridge accommodation rooms; and a plurality of airflow sources that are provided in the cartridge accommodation rooms, each of the airflow sources sending an air into the inside of the fragrance source cartridge that is accommodated in the cartridge accommodation room from the air supply port with using a diaphragm having a piezoelectric device, and each of the fragrance source cartridges comprises a container main body that has an outer shape conformed to an inner shape of the cartridge accommodation room, and is formed with an air inlet in a position corresponding to the air supply port and a fragrance outlet in a position corresponding to the air discharge port; and a solid-like fragrance source stored within the container main body, and the inner shape of the cartridge accommodation room and the outer shape of the container main body respectively have inclined surfaces inclined with respect to an insertion direction of the fragrance source cartridge.

2. The olfactory display according to claim 1, wherein the airflow source is arranged to constitute a part of the partition, and the air supply port is formed on the partition, and the cartridge exchange portion is formed on a side wall of the housing.

3. The olfactory display according to claim 1, wherein the airflow source is arranged to constitute a part of the partition, and the air supply port is formed on the partition, and the cartridge exchange portion is formed on a front wall or a rear wall of the housing.

4. The olfactory display according to claim 1, wherein the airflow source is arranged to constitute a part of a side wall and the air supply port is formed on the side wall, and the cartridge exchange portion is formed on a front wall or a rear wall of the housing.

5. The olfactory display according to claim 1, further comprising a cover that is provided in the cartridge exchange portion and pushes the fragrance source cartridge in the insertion direction when the fragrance source cartridge is accommodated in the cartridge accommodation room.

6. The olfactory display according to claim 1, wherein the emission port is formed in a plural number in a center portion at the front side of the housing, and each of the air discharge port is communicated with corresponding one of the emission ports via an individual communication hole.

7. The olfactory display according to claim 1, further comprising an auxiliary airflow source that is provided in the housing and has a diaphragm provided with a piezoelectric device.

8. A fragrance source cartridge used in the olfactory display according to claim 1, comprising:

a container main body that has an outer shape conformed to an inner shape of the cartridge accommodation room, and is formed with an air inlet in a position corresponding to the air supply port and a fragrance outlet in a position corresponding to the air discharge port; and a solid-like fragrance source stored within the container main body, wherein the outer shape of the container main body has inclined surfaces inclined with respect to an insertion direction of the fragrance source cartridge.

* * * * *